United States Patent
Barguirdjian et al.

(10) Patent No.: US 7,296,461 B2
(45) Date of Patent: *Nov. 20, 2007

(54) TEMPERATURE COMPENSATED WINDSHIELD MOISTURE DETECTOR

(75) Inventors: Pascal Barguirdjian, Saint Malo (FR); Michel Haigron, Saint Malo (FR); Allan Rex Hawk, Cheswick, PA (US); Kwaku Koi Koram, Wexford, PA (US); Shelby Chun, Mt. Lebanon, PA (US); Charles S. Voeltzel, New Kensington, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/516,769

(22) Filed: Sep. 6, 2006

(65) Prior Publication Data

US 2007/0044542 A1 Mar. 1, 2007

Related U.S. Application Data

(63) Continuation-in-part of application No. 10/963,172, filed on Oct. 11, 2004, now Pat. No. 7,204,130, which is a continuation-in-part of application No. 10/308,670, filed on Dec. 3, 2002, now Pat. No. 6,802,205.

(51) Int. Cl.
*G01N 5/02* (2006.01)

(52) U.S. Cl. .......................................................... 73/73

(58) Field of Classification Search ................. 73/73, 73/74; 318/443–448
See application file for complete search history.

(56) References Cited

U.S. PATENT DOCUMENTS

| 3,826,979 A | 7/1974 | Steinmann ................. 324/61 R |
| 4,100,398 A | 7/1978 | Levin .......................... 219/541 |

(Continued)

FOREIGN PATENT DOCUMENTS

AU    6895194    2/1995

(Continued)

OTHER PUBLICATIONS

PCT Application Serial No. PCT/US02/06163 filed Feb. 28, 2002.

(Continued)

*Primary Examiner*—Jewel Thompson
(74) *Attorney, Agent, or Firm*—Andrew C. Siminerio

(57) ABSTRACT

A moisture detection system includes an electrical conductor disposed on a surface of a substrate, an oscillator for outputting an oscillator signal at a predetermined amplitude and a predetermined frequency, and a resonator circuit coupled to the electrical conductor and responsive to the oscillator signal for outputting a resonator signal having an amplitude related to a resonant frequency of the electrical conductor. A filter circuit responsive to the resonator signal can output a rectified and filtered signal, and an analog-to-digital converter responsive to the rectified and filtered signal can output a digital signal related to the rectified and filtered signal. A sensor can be provided having a property that varies as a function of a temperature at or adjacent the electrical conductor. A controller can be responsive to the digital signal and the property of the sensor for causing another system to operate as a function thereof.

24 Claims, 7 Drawing Sheets

U.S. PATENT DOCUMENTS

| | | | |
|---|---|---|---|
| 4,323,726 A | 4/1982 | Criss et al. | 174/68.5 |
| 4,428,232 A | 1/1984 | Tanaka et al. | 73/304 C |
| 4,560,923 A | 12/1985 | Hanson | 324/61 QL |
| 4,703,237 A | 10/1987 | Hochstein | 312/483 |
| 4,748,390 A | 5/1988 | Okushima et al. | 318/483 |
| 4,827,198 A | 5/1989 | Mueller et al. | 318/483 |
| 4,859,986 A | 8/1989 | Van Auken et al. | 473/467 |
| 5,033,672 A | 7/1991 | Sakamoto et al. | 236/44 A |
| 5,598,146 A | 1/1997 | Schroder | 340/602 |
| 5,602,333 A | 2/1997 | Larrabee et al. | 73/149 |
| 5,653,904 A | 8/1997 | Adlparvar et al. | 219/203 |
| 5,659,294 A | 8/1997 | Schroder | 340/602 |
| 5,661,303 A | 8/1997 | Teder | 250/341.8 |
| 5,668,478 A | 9/1997 | Bischur | 324/690 |
| 5,672,976 A | 9/1997 | Egger et al. | 324/668 |
| 5,682,788 A | 11/1997 | Netzer | 73/73 |
| 5,694,012 A | 12/1997 | Pientka et al. | 318/444 |
| 5,703,568 A | 12/1997 | Hegyi | 340/602 |
| 5,751,071 A | 5/1998 | Netzer | 307/10.1 |
| 5,780,718 A | 7/1998 | Weber | 73/29.01 |
| 5,780,719 A | 7/1998 | VanDam | 73/29.01 |
| 5,783,743 A | 7/1998 | Weber | 73/29.01 |
| 5,801,307 A | 9/1998 | Netzer | 73/170.17 |
| 5,818,341 A | 10/1998 | Saurer et al. | 340/602 |
| 5,900,821 A | 5/1999 | Pretzold | 340/604 |
| 5,990,647 A | 11/1999 | Zettler | 318/483 |
| 6,052,196 A | 4/2000 | Pientka et al. | 356/445 |
| 6,066,933 A | 5/2000 | Ponziana | 318/483 |
| 6,084,519 A | 7/2000 | Coulling et al. | 340/602 |
| 6,094,981 A | 8/2000 | Hochstein | 73/170.17 |
| 6,118,383 A | 9/2000 | Hegyi | 340/602 |
| 6,207,967 B1 | 3/2001 | Hochstein | 250/574 |
| 6,218,741 B1 | 4/2001 | Braun et al. | 307/10.1 |
| 6,232,603 B1 | 5/2001 | Nelson | 250/339.11 |
| 6,250,148 B1 | 6/2001 | Lynam | 73/170.17 |
| 6,262,407 B1 | 7/2001 | Teder | 250/205 |
| 6,262,410 B1 | 7/2001 | Stam et al. | 250/208.1 |
| 6,268,612 B1 | 7/2001 | Teder | 250/574 |
| 6,313,457 B1 | 11/2001 | Bauer et al. | 250/214 C |
| 6,802,205 B2 * | 10/2004 | Barguirdjian et al. | 73/73 |
| 2002/0189329 A1 | 12/2002 | Wimmer | |
| 2005/0115308 A1 | 6/2005 | Koram et al. | |

FOREIGN PATENT DOCUMENTS

| | | |
|---|---|---|
| DE | 101 27 978 | 11/2002 |
| DE | 101 27 990 | 12/2002 |
| DE | 101 28 010 | 1/2003 |
| EP | 0 308 990 | 3/1989 |
| EP | 0 638 822 | 2/1995 |
| EP | 0 890 143 B1 | 12/2001 |
| EP | 1 264 746 | 5/2002 |
| JP | 55063940 A | 5/1980 |
| JP | 04184226 A | 7/1992 |
| JP | 09043187 | 2/1997 |
| WO | WO98/30922 | 7/1998 |
| WO | 01/81931 A1 | 11/2001 |
| WO | WO2004/050442 | 6/2004 |
| WO | 2005/029134 A1 | 3/2005 |
| WO | WO 2006/122942 | 11/2006 |
| WO | WO 2006/122943 | 11/2006 |

OTHER PUBLICATIONS

International Search Report mailed Sep. 9, 2004.
International Search Report and Written Opinion of the International Searching Authority mailed on Feb. 20, 2006, corresponding to International Application No. PCT/US2005/036486, filed Oct. 11, 2005.

* cited by examiner

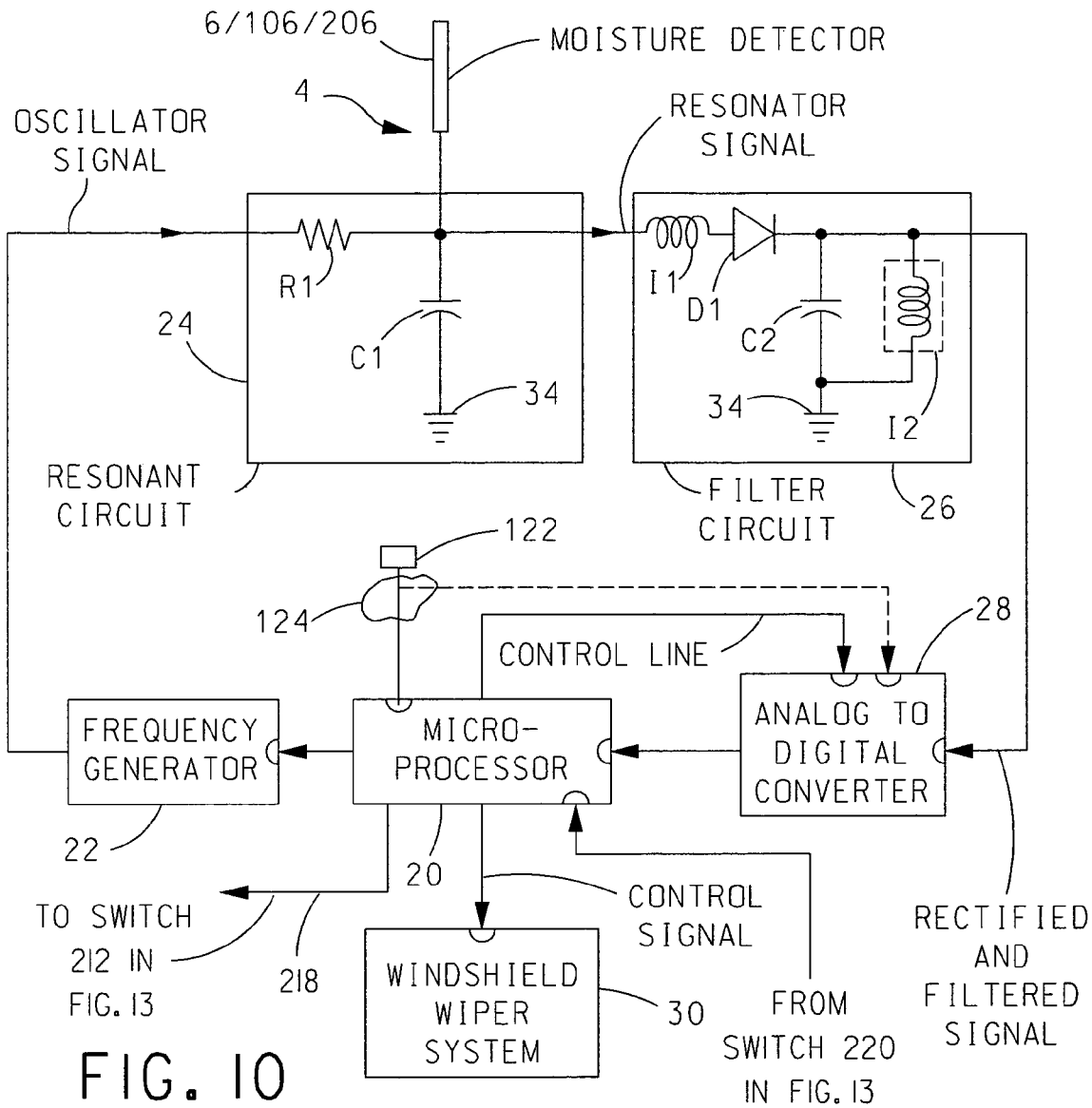

TEMPERATURE COMPENSATED WINDSHIELD MOISTURE DETECTOR

This application is a continuation-in-part of U.S. patent application Ser. No. 10/963,172, filed Oct. 11, 2004, now U.S. Pat. No. 7,204,130 entitled WINDSHIELD MOISTURE DETECTOR, which is a continuation-in-part of U.S. patent application Ser. No. 10/308,670, filed Dec. 3, 2002, now U.S. Pat. No. 6,802,205, entitled MOISTURE DETECTION SYSTEM AND METHOD OF USE THEREOF, both of which are incorporated herein by reference.

BACKGROUND OF THE INVENTION

1. Field of the Invention

The present invention relates to moisture detection and, more particularly, to moisture detection on a vehicle windshield.

2. Description of the Prior Art

Heretofore, the detection of moisture on a windshield of a vehicle was accomplished in four basic manners: capacitive sensor systems, resistive sensor systems, ultrasonic sensor systems and optical sensor systems.

A capacitive sensor system includes a capacitor formed on the windshield. In response to moisture on the windshield, the capacitance of the capacitor changes. A sensing circuit is connected to detect the changing capacitance and to control the operation of a windshield wiper as a function of the changing capacitance. Examples of capacitive moisture sensors include U.S. Pat. No. 5,668,478 to Buschur; U.S. Pat. No. 5,682,788 to Netzer; U.S. Pat. No. 5,801,307 to Netzer; and U.S. Pat. No. 6,094,981 to Hochstein.

A resistive measurement system includes two conductive elements disposed in spaced relation on the windshield, or another part of the vehicle, such as a conventional whip antenna. Circuitry coupled to the conductive elements measures a change in resistance thereof in response to water bridging the resistive elements and controls the operation of the windshield wiper as a function of the change in resistance. Examples of resistive measurement systems include U.S. Pat. No. 5,659,294 to Schroder; U.S. Pat. No. 5,598,146 to Schroder; U.S. Pat. No. 5,780,718 to Weber; U.S. Pat. No. 5,780,719 to VanDam; U.S. Pat. No. 5,783,743 to Weber; and U.S. Pat. No. 5,900,821 to Petzold.

An ultrasonic sensor system includes a transducer that emits an ultrasonic signal toward a first face of a sheet and receives a reflected ultrasonic signal on a second face of the sheet. The variation in the reflected signal is utilized to determine the presence or absence of foreign bodies on the second face of the sheet. Examples of ultrasonic sensor systems include U.S. Pat. No. 5,818,341 to Saurer et al. and European Publication No. EP0638822.

An optical sensor system includes a light detector positioned to detect light reflected off a windshield from a light source. In response to the presence of moisture on the windshield, the amount of light detected by the light sensor will change due to changing reflection of the light from the light source, thus causing a change in the output of the light sensor. Detecting circuitry detects the change in output from the light detector in response to the change in light impinging thereon and operates the windshield wiper as a function of the change. Examples of light detecting systems include U.S. Pat. No. 5,694,012 to Pientka et al.; U.S. Pat. No. 5,990,647 to Zettler; U.S. Pat. No. 6,052,196 to Pientka et al.; U.S. Pat. No. 6,066,933 to Ponziana; U.S. Pat. No. 6,084,519 to Coulling et al.; U.S. Pat. No. 6,207,967 to Hochstein; U.S. Pat. No. 5,661,303 to Teder; U.S. Pat. No. 6,250,148 to Lynam; U.S. Pat. No. 6,218,741 to Braun et al.; and U.S. Pat. No. 6,232,603 to Nelson.

A problem with a capacitive sensor system includes the need to form a capacitor having sufficient capacitance whereupon the change in capacitance in response to the presence of rain on the windshield can be detected by suitable detection circuitry. Another problem with a capacitive sensor system is the change in capacitance due to heating or cooling of the metal films forming the capacitor thereby resulting in a change in the capacitance of the capacitor during use.

A problem with a resistive sensor system includes the need to have the resistive elements formed on the outer surface of the windshield whereupon the resistive elements are exposed to weather and possible deterioration. In addition, the resistive elements of a resistive sensor system are also subject to changes in resistance due to changes in the temperature.

A problem with an ultrasonic sensor system and an optical sensor system includes the need to position the transducer of the ultrasonic sensor system and the light transmitter and light receiver of the optical sensor system inside the vehicle to detect the presence of moisture at a suitable location on the windshield. However, positioning the ultrasonic sensor system or the optical sensor system at a suitable location on the windshield often results in partially blocking a driver's view through the windshield or in the positioning of such sensor system at less than an optimal location for detecting the presence of moisture on the windshield. Moreover, the sensitivity of an optical sensor to detect moisture can be compromised by the color or shade of the windshield in the path of the light propagating from the light transmitter to the light receiver.

It would, therefore, be desirable to provide a small, nearly invisible, moisture detector disposed on either a flexible substrate that is coupled to a sheet, such as a windshield, or on the sheet itself. The moisture detector can be coupled to circuitry for stimulating the moisture detector and circuitry for detecting a change in a characteristic of the moisture detector due to the presence of moisture on the sheet. It would also be desirable to provide a method for detecting the change of the characteristic of the moisture detector as a function of the temperature of the sheet.

SUMMARY OF THE INVENTION

The invention is a moisture detection system that includes an electrical conductor disposed on a surface of a substrate. The electrical conductor has a resonant frequency that varies as a function of an amount of moisture present adjacent the electrical conductor. An oscillator outputs an oscillator signal at a predetermined amplitude and a predetermined frequency. A resonator circuit is coupled to the electrical conductor and is responsive to the oscillator signal for outputting a resonator signal having an amplitude related to the resonant frequency of the electrical conductor. A filter circuit is responsive to the resonator signal for outputting a rectified and filtered signal. An analog-to-digital converter is responsive to the rectified and filtered signal for outputting a digital signal related to the rectified and filtered signal. A sensor is provided that has a property that varies as a function of a temperature at or adjacent the electrical conductor is provided. A controller is responsive to the digital signal and the property of the sensor for causing another system to operate as a function thereof.

The other system can be a wiper system that is responsive to the controller for adjusting a rate moisture is removed from adjacent the electrical conductor as a function of an amount of moisture present adjacent the electrical conductor and/or a rate moisture accumulates adjacent the electrical conductor. The wiper system can include a means for wiping.

The wiper system can be responsive to the digital signal and the property of the sensor for causing the wiping means to remove moisture from a surface.

The predetermined frequency can be between (i) 300 and 700 kHz or (ii) 400 and 600 kHz.

The substrate can be a vehicle windshield having a plurality of transparent sheets laminated together and the electrical conductor can be sandwiched between the sheets.

The substrate can be a flexible substrate. The vehicle windshield can have a plurality of transparent sheets laminated together with the flexible substrate sandwiched between the transparent sheets. An electrically conductive coating can be disposed on a surface of at least one transparent sheet. Said surface can be a side of the flexible substrate opposite the electrical conductor. The flexible substrate can further include (i) a ground conductor disposed on the flexible substrate at least partially surrounding the electrical conductor or (ii) a conductive material, in the form of a faraday shield, disposed on a surface of the flexible substrate opposite the electrical conductor.

The resonator circuit can include a capacitor connected between the electrical conductor and a reference voltage and a resistor connected between the oscillator and the electrical conductor side of the capacitor. The filter circuit can include a diode connected to conduct current from the resonator toward the analog-to-digital converter and a capacitor connected between an end of the diode adjacent the analog-to-digital converter and the reference voltage.

The invention is also a moisture detector system that includes means disposed on a substrate for conducting electrical current, the conducting means having a resonant frequency that changes as a function of moisture adjacent the conducting means; an oscillator for outputting to the conducting means an oscillator signal having a predetermined frequency and a first amplitude; means responsive to the oscillator signal for outputting a resonator signal having a second amplitude related to the resonant frequency of the conducting means, wherein the second amplitude is different than the first amplitude; means having a property whose value varies as a function of a temperature at or adjacent the conducting means; and means responsive to the resonator signal and the value of the property for outputting a control signal having a value related to the second amplitude of the resonator signal.

The moisture detector can further include a wiper system responsive to the control signal for wiping moisture from adjacent the conducting means based on an amount of moisture adjacent the conducting means and/or a rate moisture accumulates adjacent the conducting means.

The conducting means can include (i) one or more lines of conductive material, (ii) one or more sheets of conductive material, and/or (iii) a dispersion of conductive particles in the form of one or more lines and/or sheets.

The substrate can be a windshield that includes plural sheets of glass laminated together. The conducting means can be sandwiched between the sheets of glass.

The substrate can be a flexible substrate that is coupled to a sheet and the conducting means can have a resonant frequency that changes as a function of moisture on the sheet.

The moisture detector can further include a wiper system disposed in operative relation to the sheet and responsive to the control signal for wiping the sheet based on an amount of moisture on the sheet and/or a rate moisture accumulates on the sheet.

The conducting means can include one or more lines of electrically conductive material disposed on the flexible substrate.

The sheet can be a windshield that includes plural sheets of glass laminated together.

The flexible substrate can be sandwiched between the sheets of glass.

The flexible substrate can further include (i) a ground conductor disposed on the flexible substrate at least partially surrounding the conducting means or (ii) a conductive material disposed on a surface of the flexible substrate opposite the conducting means, said conductive material having a form that defines a faraday shield.

The moisture detector can further include an electrically conductive coating disposed on a surface of at least one sheet. The surface can be positioned on a side of the flexible substrate opposite the conducting means.

The invention is also a method of moisture detection comprising (a) providing a substrate having an electrical conductor disposed thereon; (b) stimulating the electrical conductor with an oscillator signal in the absence of moisture adjacent the electrical conductor; (c) detecting a value of a temperature dependent property acquired from a location at or adjacent the electrical conductor on or about the time step (b) is performed; (d) determining a first amplitude of the electrical conductor to the stimulation in step (b) as a function of the value of the temperature dependent property detected in step (c); (e) stimulating the electrical conductor with the oscillator signal when moisture is present adjacent the electrical conductor; (f) detecting the value of the temperature dependent property on or about the time step (e) is performed; (g) determining a second amplitude of the electrical conductor to the stimulation in step (e) as a function of the value of the temperature dependent property detected in step (f), wherein the second amplitude is different than the first amplitude due to a change in resonant frequency of the electrical conductor in response to the presence of moisture adjacent the electrical conductor; and (h) determining a difference between the first amplitude and the second amplitude, wherein the difference is related to the amount of moisture present adjacent the electrical conductor.

The detected temperature dependent property can be physically or optically detected. The physically detected property can be voltage, current or resistance. More specifically, the detected temperature dependent property can be a potential output by a bimetallic junction acting as the temperature sensor, a resistance of a thermistor or a conductor acting as the temperature sensor, or a signal output by an optical temperature sensor acting as the temperature sensor.

The method can further include removing moisture from adjacent the electrical conductor at a rate related to the difference between the first amplitude and the second amplitude.

The method can further include sandwiching the substrate between at least two sheets of glass. Shielding means can be provided on (i) the substrate and/or (ii) at least one of the sheets of glass. The substrate can be flexible.

The invention is also a moisture detection system that includes a substrate, an electrical conductor disposed on the substrate, means for stimulating the electrical conductor with an oscillator signal, means for detecting a temperature at or adjacent the electrical conductor; and means responsive to the oscillator signal, the electrical conductor and the detected temperature for determining temperature corrected changes in a resonant frequency of the electrical conductor in response to changes in an amount of moisture disposed adjacent the electrical conductor.

A sheet can be in contact with the substrate. The system can further include means for removing an accumulation of moisture on the sheet; and means responsive to the determining means for controlling when the removing means removes the accumulation of moisture from the sheet.

The substrate can be disposed on (i) a side of the sheet receiving the accumulation of moisture or (ii) a side of the sheet not receiving the accumulation of moisture. The sheet can be formed from a plurality of sheets joined together.

The invention is also a method of moisture detection comprising correcting a value of a signal generated in response to the presence of moisture on a substrate as a function of a temperature detected at or adjacent the substrate and controlling a system as a function of the corrected signal.

The invention is also a method of moisture detection comprising generating a signal having a value related to an amount of moisture on a substrate, combining the signal with a correction factor related to a temperature at or adjacent the substrate and controlling a system as a function of the combination.

The invention is also a moisture detection system comprising a substrate; a resistive conductor disposed on the substrate; a source of DC power; means for generating an AC oscillator signal; means for applying the DC power and the AC oscillator signal one at a time to the resistive conductor; and means responsive to the application of the oscillator signal to the resistive conductor for determining changes in a resonant frequency of the resistive conductor in response to changes in an amount of moisture disposed adjacent the resistive conductor.

The system can includes means for removing an accumulation of moisture on the sheet; and means responsive to the determining means for controlling when the removing means removes the accumulation of moisture from the sheet.

Lastly, the invention is a method of moisture detection comprising (a) connecting a resistive conductor to a source of DC power; (b) disconnecting the resistive conductor from the source of DC power; (c) connecting the resistive conductor to an AC signal source; (d) in response to the application of the AC signal source, determining a change in a resonant frequency of the resistive conductor related to a change in an amount of moisture adjacent the resistive conductor; and (e) removing moisture from adjacent the resistive conductor as a function of the change in the resonant frequency thereof.

Step (e) of the method can also include removing moisture from adjacent the resistive conductor as a function of a temperature adjacent the resistive conductor.

BRIEF DESCRIPTION OF THE DRAWINGS

FIG. 10 is a schematic drawing of circuitry utilized to stimulate and detect the response of any one of the embodiments of the moisture detectors disclosed herein;

FIG. 11 is a schematic drawing of the windshield wiper system shown in FIG. 10;

DETAILED DESCRIPTION OF THE INVENTION

Figure 1:
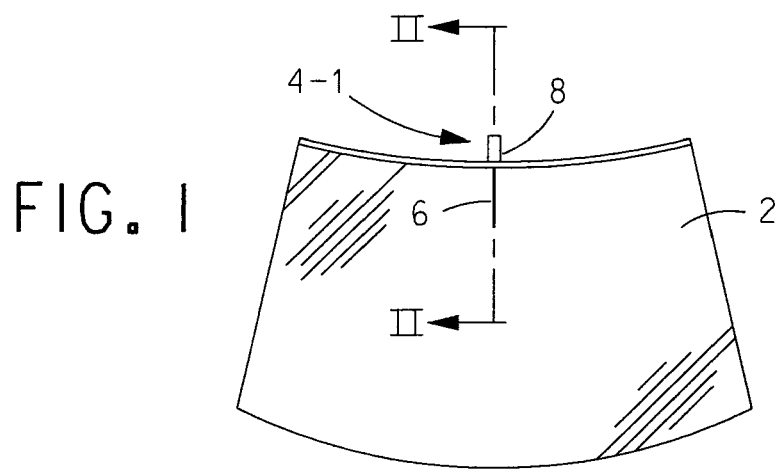
FIG. 1 is a plan view of a sheet, such as a sheet of glass or a windshield, including a first nonlimiting embodiment of a moisture detector for detecting moisture on the sheet incorporating features of the present invention.

The present invention will be described with reference to the accompanying figures where like reference numbers correspond to like elements.

As used herein, spatial or directional terms, such as "inner", "outer", "left", "right", "up", "down", "horizontal", "vertical", and the like, relate to the invention as it is shown in the drawing figures. However, it is to be understood that the invention can assume various alternative orientations and, accordingly, such terms are not to be considered as limiting. Further, all numbers expressing dimensions, physical characteristics, and so forth, used in the specification and claims are to be understood as being modified in all instances by the term "about". Accordingly, unless indicated to the contrary, the numerical values set forth in the following specification and claims can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, and all subranges in between. Also, as used herein, terms such as "positioned on" or "supported on" mean positioned or supported on but not necessarily in direct surface contact with. For example, a substrate "positioned on" a glass sheet does not preclude the presence of one or more other materials located between the substrate and the surface of the sheet.

With reference to FIG. 1, a sheet or panel of optically transparent material, such as a sheet of glass or a vehicle windshield 2, includes a moisture detector 4 disposed thereon or incorporated therein. In a first nonlimiting embodiment of the present invention, moisture detector 4-1 includes one or more electrical conductors 6 connected to a connector, e.g. conductive foil 8, which is utilized for connecting electronic circuitry to electrical conductor 6. In the nonlimiting embodiment shown in FIG. 1, foil 8 is shown extending outside the periphery of windshield 2. However, this is not to be construed as limiting the invention since foil 8 may be disposed entirely within the periphery of windshield 2.

Figure 2:
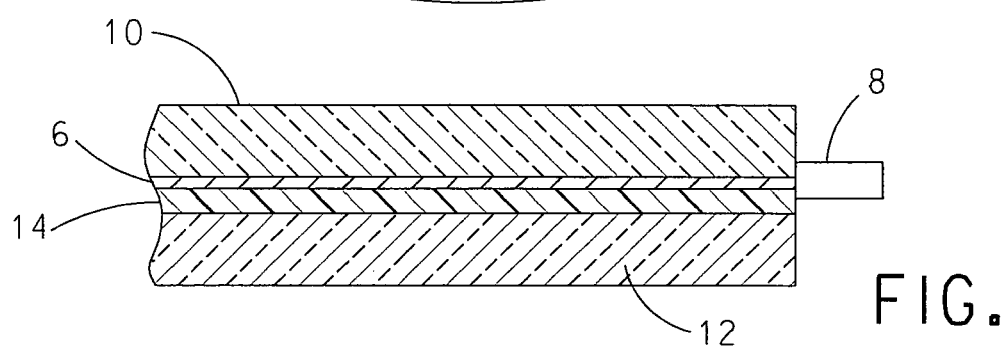
FIG. 2 is a cross section taken along lines II-II in FIG. 1.

With reference to FIG. 2, and with continuing reference to FIG. 1, windshield 2 is desirably formed by outer and inner glass plies 10 and 12 bonded together by a plastic interlayer 14, such as polyvinylbutyral, to form windshield 2 as a unitary structure. Plies 10 and 12, however, may be other transparent rigid material, such as, but not limited to, polycarbonate. Each electrical conductor 6 can be disposed on an inward or an outward facing surface of glass ply 10 or glass ply 12. Each electrical conductor 6 can be a conductive wire or sheet, or a conductive coating applied to one of the surfaces of glass ply 10 or glass ply 12 in the form of a line or a sheet, or a dispersion of electrically conductive particles applied to one of the surfaces of glass ply 10 or glass ply 12 in the form of a line or a sheet. Although not required, each electrical conductor 6 has a width and/or thickness that renders it not easily discernable to the naked eye. In one nonlimiting embodiment of the invention, the width of the electrical conductors 6 is no greater than 0.35 mm, for example no greater than 0.30 mm or no greater than 0.25 mm.

Figure 3:
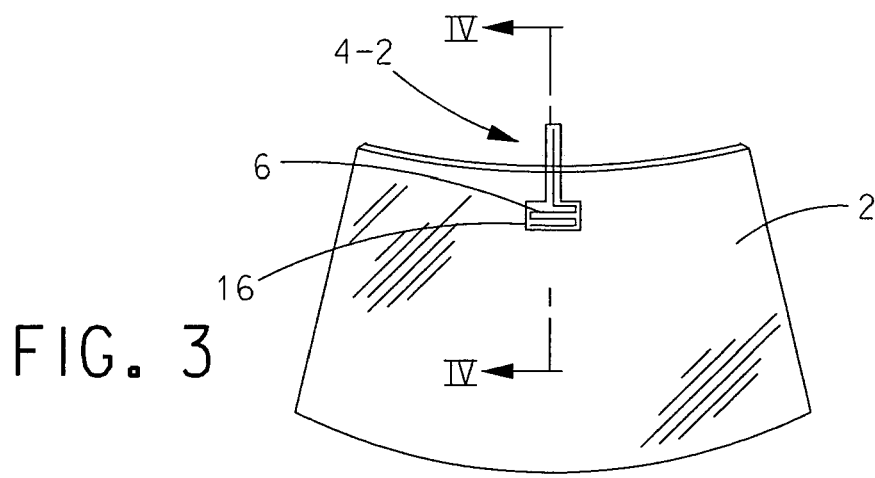
FIG. 3 is a plan view of a sheet, such as a sheet of glass or a windshield, including a second nonlimiting embodiment of a moisture detector for detecting moisture on the sheet incorporating features of the present invention.
Figure 4:
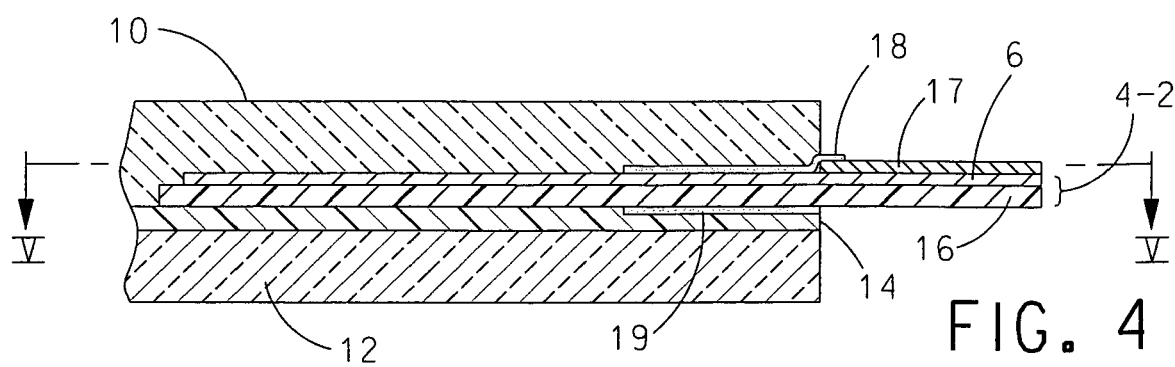
FIG. 4 is a cross section taken along lines IV-IV in FIG. 3.
Figure 5:
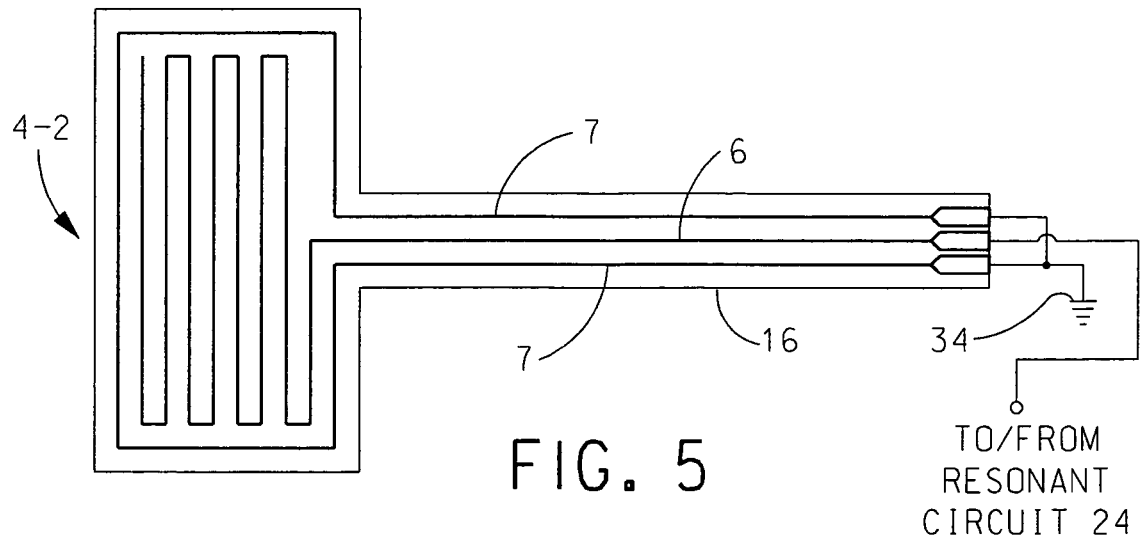
FIG. 5 is a view taken along lines V-V in FIG. 4, with portions removed for clarity.

With reference to FIGS. 3-5, in a second nonlimiting embodiment, moisture detector 4-2 includes one or more electrical conductors 6 disposed on a flexible substrate 16. In FIGS. 3 and 4, part of flexible substrate 16 including electrical conductor(s) 6 disposed thereon extends outside the periphery of windshield 2 to facilitate connection of electronic circuitry to electrical conductor(s) 6. However, this is not to be construed as limiting the invention since flexible substrate 16 having electrical conductor(s) 6 disposed thereon may be disposed entirely within the periphery of windshield 2.

As shown in FIG. 4, flexible substrate 16 can be sandwiched between glass plies 10 and 12 with electrical conductor 6 facing an inward facing surface of glass ply 10 or glass ply 12, or one of the outward facing surfaces of plastic interlayer 14. Alternatively, flexible substrate 16 can be disposed on an outward facing surface of glass ply 10 or glass ply 12 with electrical conductor 6 facing toward or away from said outward facing surface. As another alternative, the flexible substrate 16 can be incorporated within the interlayer 14. Although not required, to avoid undesirable exposure of flexible substrate 16 and/or electrical conductor(s) 6 to, among other things, moisture and/or particulate contaminant(s), it is desirable to position flexible substrate 16 between glass plies 10 and 12 versus positioning flexible substrate 16 on an outward facing surface of glass ply 10 or glass ply 12.

Flexible substrate 16 can be formed from any suitable flexible and insulative material, such as, but not limited to, polyethyleneterephthalate (PET), polyvinylbutyral (PVB), ultra-thin glass, etc. In one nonlimiting embodiment, substrate 16 is 2 mil thick PET. A desired pattern of electrical conductor(s) 6 can be formed from a sheet of any suitable electrically conductive material adhered to flexible substrate 16 utilizing conventional photolithographic processing techniques. The desired pattern of electrical conductor(s) 6 can also be formed on flexible substrate 16 by screen printing a suitable conductive material in the desired pattern on flexible substrate 16 or by ink jetting a suitable conductive material in the desired pattern on flexible substrate 16. The desired pattern of electrical conductor(s) 6 can also be formed on flexible substrate 16 by a wire, such as, but not limited to, copper wire, secured to or embedded within the substrate 16. Although not required, in one nonlimiting embodiment, the wire has a small diameter so that the wire is less visible in the windshield 2. In one nonlimiting embodiment, the wire is 36 AWG tin plated copper wire. As discussed above, it should be appreciated that rather than using a flexible substrate, the conductors 6 can be applied directly to a surface of the glass plies or interlayer. For example, and without limiting the present invention, rather than combining the wire with the substrate 16, the wire can be secured to or embedded within the interlayer 14. The foregoing methods of forming the pattern of electrical conductor(s) 6 on flexible substrate 16 are not to be construed as limiting the invention since the use of any suitable means for forming the desired pattern of electrical conductor(s) 6 on flexible substrate 16 is envisioned.

Figure 6:
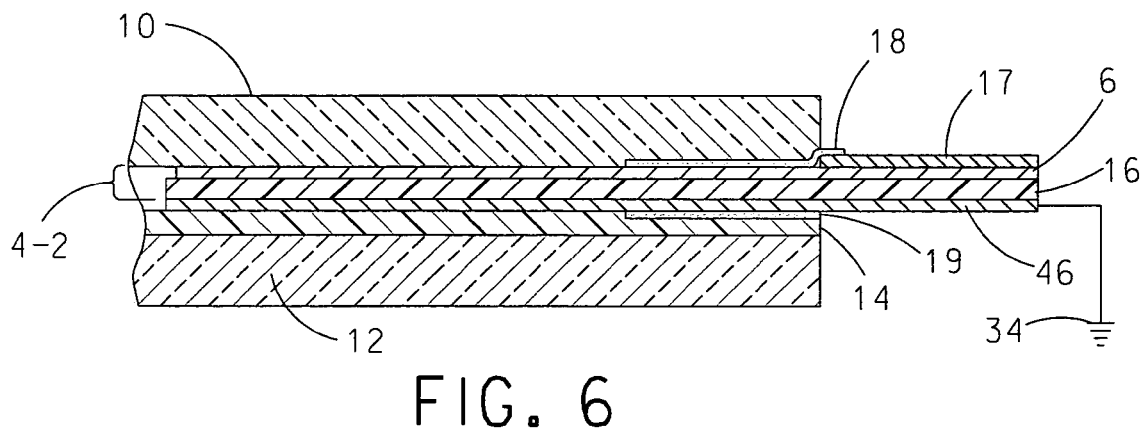
FIG. 6 is a cross section of the second embodiment moisture detector shown in FIG. 4 including a conductive material positioned on a side of the substrate opposite the electrical conductor.

With reference to FIGS. 5 and 6, and with continuing reference to FIGS. 3 and 4, the portion of flexible substrate 16 extending outside the periphery of windshield 2 can have electrical conductor(s) 6 sandwiched between flexible substrate 16 and an insulative material 17 adhered to electrical conductor(s) 6. Insulative material 17 can be formed from a sheet of suitable insulative material, such as, without limitation, Kapton® polyimide film (Kapton® is a registered trademark of E.I. DuPont de Nemoirs and Company Corporation, Wilmington, Del.), or any other suitable solid or flowable insulative material that acts to protect electrical conductor(s) 6. Since the portions of electrical conductor(s) 6 and substrate 16 sandwiched between glass plies 10 and 12 are protected thereby from moisture and/or particulate contaminant(s), an end of insulative material 17 can terminate between glass plies 10 and 12.

To avoid exposure of electrical conductor(s) 6 sandwiched between glass plies 10 and 12 to moisture and/or particulate contaminant(s), an adhesive 18, e.g., a thermoset adhesive, can be disposed on the electrical conductor 6 side of flexible substrate 16 positioned between glass plies 10 and 12. This adhesive 18 covers the end of insulative material 17 sandwiched between glass plies 10 and 12 and extends between glass plies 10 and 12 a sufficient distance so that when it is cured, adhesive 18 forms with glass plies 10 and 12 and plastic interlayer 14 a hermetic seal that inhibits moisture and/or particulate contaminant(s) from contacting the portion of electrical conductor(s) 6 sandwiched between glass plies 10 and 12.

Another adhesive 19, e.g., a pressure sensitive adhesive, can be disposed between flexible substrate 16 and plastic interlayer 14 for securing the position of flexible substrate 16 between glass plies 10 and 12 prior to exposing adhesive 18 and plastic interlayer 14 to a curing heat.

As shown in FIG. 5, flexible substrate 16 can include a ground conductor 7 that at least partially surrounds electrical conductor(s) 6. Connecting ground conductor 7 to an external reference voltage 34, such as ground, forms a ground loop around electrical conductor(s) 6. This ground loop avoids undesirable electromagnetic interference from affecting the operation of electrical conductor(s) 6 acting as a resonating element of moisture detector 4-2. Moreover, as shown in FIG. 6, a side of flexible substrate 16 opposite electrical conductor(s) 6 can also or alternatively include a conductive material 46 disposed thereon that can be connected to external reference voltage 34. Conductive material 46 can be in the form of a sheet, one or more lines, a mesh, or any other suitable form that defines a faraday shield that avoids undesirable electromagnetic interference from affecting the operation of electrical conductor(s) 6 acting as the resonating element of moisture detector 4-2.

Figure 7:
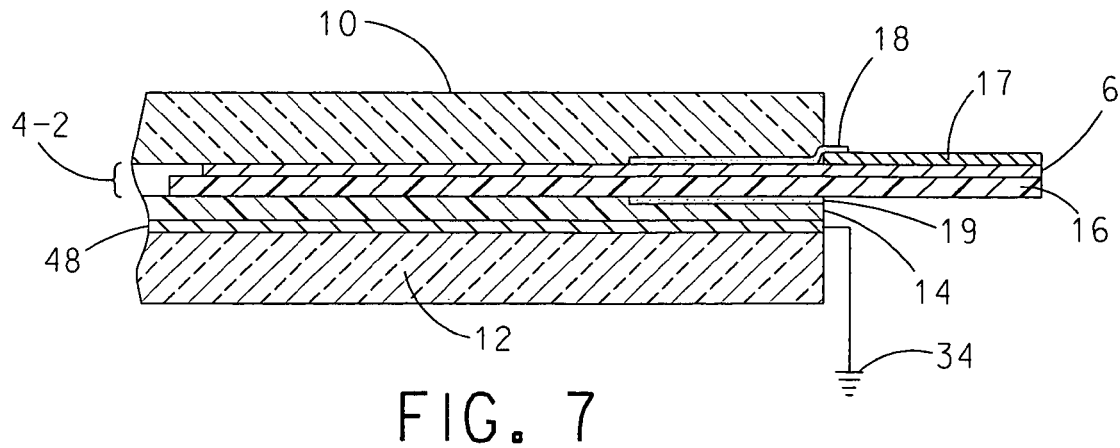
FIG. 7 is a cross section of the second embodiment moisture detector shown in FIG. 4 including an electrically conductive coating on the inside surface of one of the sheets of glass.

With reference to FIG. 7, and with continuing reference to FIGS. 3-6, an electrically conductive coating 48 can also or alternatively be formed on a surface, e.g., inner surface, of glass ply 12 and connected to reference voltage 34 for avoiding undesirable electromagnetic interference from affecting the operation of electrical conductor(s) 6 acting as the resonating element of moisture detector 4-2. Electrically conductive coating 48 can be transparent or colored. When colored, electrically conductive coating 48 can serve the dual purpose of a ground plane or faraday shield for moisture detector 4-2 and a sun shade of windshield 2. While described in connection with the second embodiment moisture detector 4-2, it is to be appreciated that electrically conductive coating 48 can also be disposed on a surface, e.g., inner surface, of glass ply 12 when utilized with the first embodiment moisture detector 4-1 shown in FIGS. 1 and 2. As can be seen, any one or a combination of ground conductor 7, conductive material 46 and/or electrically conductive coating 48 can be utilized for avoiding undesirable electromagnetic interference from affecting the operation of electrical conductor(s) 6 acting as the resonating element of moisture detector 4-2.

Alternatively, substrate 16 can be omitted and one or more of conductor(s) 6 and 7 comprising the second embodiment moisture detector 4-2 can be disposed directly on one or more surfaces of glass ply 10, glass ply 12 and/or interlayer 14 in any desired arrangement deemed suitable by one of ordinary skill in the art. Electrically conductive coating 48 can also be utilized in combination with conductor(s) 6 and/or 7 of the second embodiment moisture detector 4-2 when conductor(s) 6 and/or 7 are disposed directly on one or more surfaces of glass ply 10, glass ply 12 and/or interlayer 14.

Figure 8:
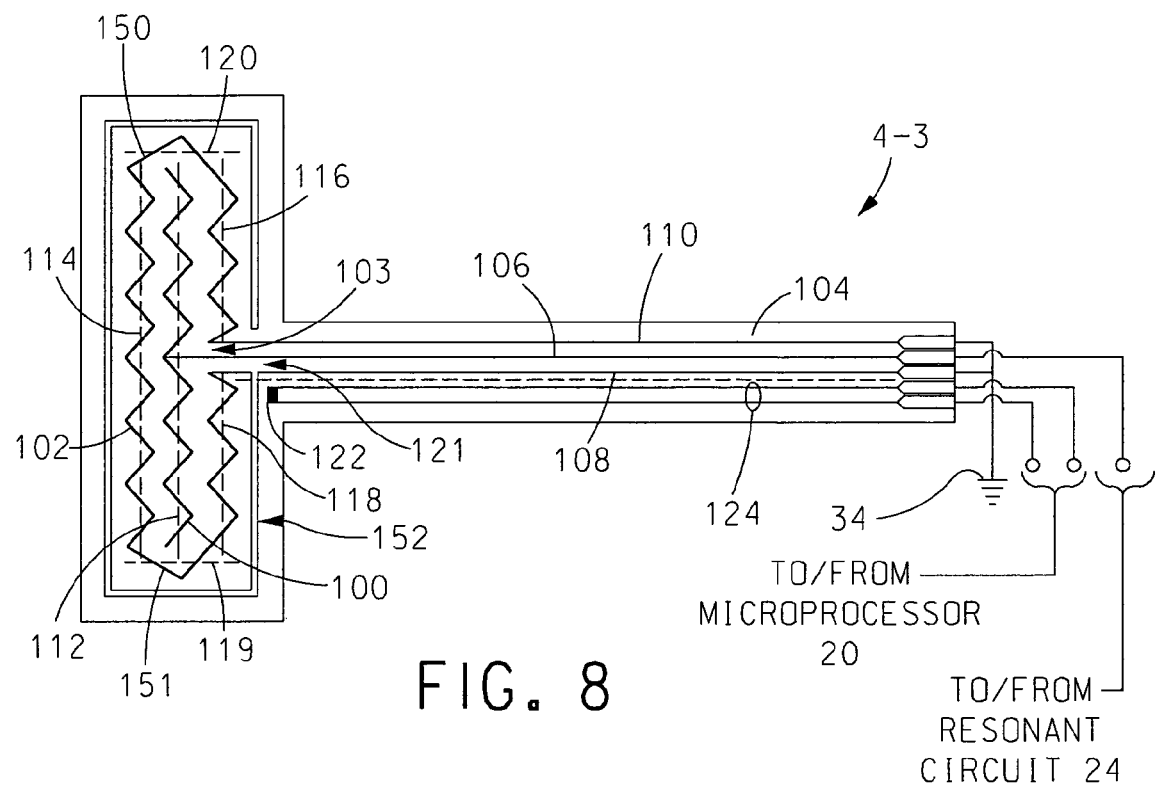
FIG. 8 is a plan view similar to that shown in FIG. 5 of a third nonlimiting embodiment of a moisture detector for detecting moisture on a sheet incorporating features of the present invention.

With reference to FIG. 8, and with continuing reference to FIGS. 1-7, in a third nonlimiting embodiment of the present invention, moisture detector 4-3 includes a first elongated electrical conductor 100 and a second elongated electrical conductor 102 disposed on a flexible substrate 104. Second conductor 102 can at least partially surround first conductor 100 defining a gap 103 between the ends of second conductor 102. A power conductor 106 can also be disposed on substrate 104. Power conductor 106 is electrically connected to first conductor 100 via gap 103 between the ends of second conductor 102. In the particular nonlimiting embodiment illustrated in FIG. 8, conductor 106 is electrically connected to conductor 100 intermediate the ends of conductor 100. A ground conductor 108 can also be disposed on substrate 104. Ground conductor 108 is electrically connected to one end of second conductor 102. Another ground conductor 110 can be disposed on substrate 104 and can be electrically connected to the other end of second conductor 102.

First conductor 100 defines a longitudinal axis 112 and at least the portion of second conductor 102 disposed on a side of first conductor 100 opposite gap 103 defines a longitudinal axis 114 that is positioned in spaced relation with longitudinal axis 112 of first conductor 100. The portions of second conductor 102 on opposite sides of gap 103 also define longitudinal axes 116 and 118 that are positioned in spaced relation with longitudinal axis 112 of first conductor 100. Longitudinal axes 112-118 are shown in phantom in FIG. 8. In the particular nonlimiting embodiment illustrated in FIG. 8, first conductor 100 and second conductor 102 define zigzag paths along their longitudinal axes 112 and 114-118. As used herein, "zigzag" means a series of short, sharp turns or angles resulting in a plurality of distinct points along the path of the conductor. Although not required, these zigzag paths can track each other in substantially spaced relation along their longitudinal axes. Although not required, in the particular embodiment of the moisture detector shown in FIG. 8, longitudinal axes 114, 116 and 118 are substantially parallel to longitudinal axis 112 and the zigzag paths track each other in substantially parallel spaced relation.

It is believed that the zigzag path of the conductors as discussed above increases the sensitivity of the moisture detector by providing multiple electric field emitting points along its length. More specifically, it has been observed that a straight conductor element used as a moisture detecting element in one embodiment of the moisture detector of the present invention will have a higher electric field strength at the ends of the element as compared to the electric field strength along its length. By forming the conductors in a zigzag pattern, additional distinct points or tips are formed along its length. At each of these points, the element will have a higher electric field strength as compared to a straight portion of the element, thus creating more sensitive transmitting points in the same overall distance as the straight element. As a result of the more sensitive transmitting points with higher field strength, water drops deposited along the length of the zigzag pattern will cause relatively larger changes in impedance of the moisture detector element and hence would be more detectable in comparison to deposition on the straight line pattern.

Portions 150 and 151 of second conductor 102 spaced from opposite ends of first conductor 100 define longitudinal axes 119 and 120 (shown in phantom), which in the nonlimiting embodiment shown in FIG. 8, are positioned substantially perpendicular to longitudinal axis 112 of first conductor 100. As shown, portions 150 and 151 of second conductor 102 define zigzag paths spaced from the opposite ends of first conductor 100. Although not required, in this particular embodiment portions 119 and 120 are mirror images of each other.

In one nonlimiting embodiment, ground conductor 108 defines a straight line connection to second conductor 102, as shown by the phantom line adjacent ground conductor 108. Optionally, ground conductor 108 at least partially surrounds second conductor 102 as shown in FIG. 8. In the illustrated nonlimiting embodiment of moisture detector 4-3, the optional configuration of ground conductor 108 has a generally rectangular form 152 surrounding second conductor 102. However, this is not to be construed as limiting the invention. The optional configuration of ground conductor 108 defines a gap 121 for passage of power conductor 106 for electrical connection to first conductor 100. Gap 121 can also be used for the passage of ground conductor 110 for electrical connection to second conductor 102.

Optionally, a temperature sensor 122 is disposed at or adjacent moisture detector 4-3, or any other moisture detector 4, e.g., on substrate 104 in close proximity to first and second conductors 100 and 102, respectively. One or more conductors 124 are connected to temperature sensor 122 to facilitate connection of sensor 122 to suitable sensing circuitry, such as a microprocessor 20 or an analog-to-digital converter 28 (the latter connection shown in phantom), both described hereinafter, as required.

Substrate 104 of the third embodiment moisture detector 4-3 can be formed from the same material(s) as substrate 16 of the second embodiment moisture detector 4-2. The pattern of conductors 100, 102, 106, 108, 110 and 124 can also be formed on flexible substrate 104 in the manner described in connection with the formation of conductor(s) 6 and 7 on substrate 16 of the second embodiment of moisture detector 4-2. Accordingly, details regarding how the pattern of electrical conductors 100, 102, 106, 108 and 110 and 124 are formed on substrate 104 will not be described herein to avoid unnecessary redundancy.

Third embodiment moisture detector 4-3 including substrate 104 can be sandwiched between glass plies 10 and 12 in the manner discussed above in connection with the second embodiment moisture detector 4-2. Conductive material 46 can be disposed on substrate 104 in the manner described above in connection with moisture detector 4-2 to avoid undesirable electromagnetic interference from affecting the operation of moisture detector 4-3. Similarly, electrically conductive coating 48 can be utilized with third embodiment moisture detector 4-3 in the manner described above in connection with second embodiment moisture detector 4-2 including substrate 104.

Alternatively, substrate 104 can be omitted and the conductors comprising third embodiment moisture detector 4-3 can be disposed directly on one or more surfaces of glass ply 10, glass ply 12 and/or interlayer 14 in any desired arrangement deemed suitable by one of ordinary skill in the art. In one nonlimiting embodiment of the present invention, temperature sensor 122 is disposed on the same surface of glass ply 10, glass ply 12, interlayer 14 or substrate 104 as the conductors of third embodiment moisture detector 4-3 and positioned at or adjacent detector 4-3. Electrically conductive coating 48 can also be utilized with third embodiment moisture detector 4-3 where the conductors thereof are disposed directly on one or more surfaces of glass ply 10, glass ply 12 and/or interlayer 14.

Figure 9:
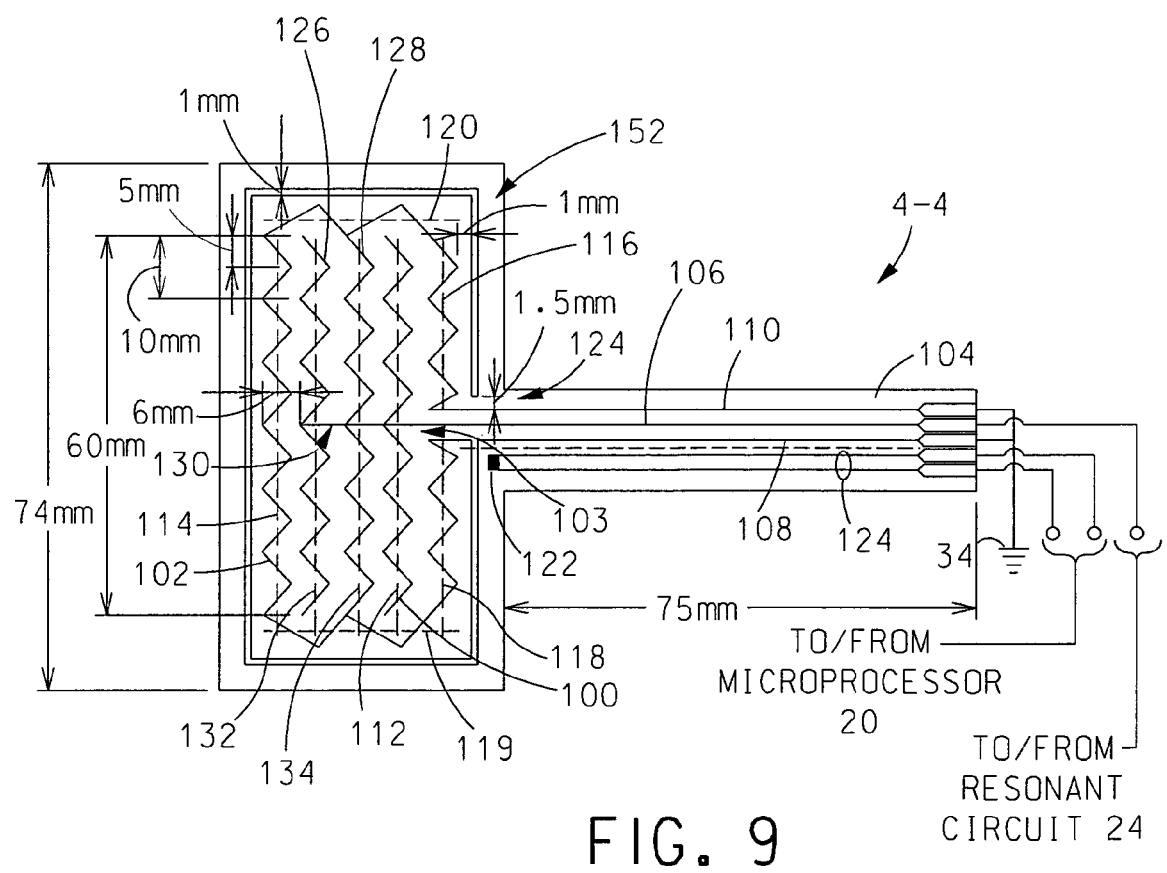
FIG. 9 is a plan view similar to that shown in FIG. 5 of a fourth nonlimiting embodiment of a moisture detector for detecting moisture on a sheet incorporating features of the present invention.

With reference to FIG. 9, and with continuing reference to FIGS. 1-8, in a fourth nonlimiting embodiment of the present invention, moisture detector 4-4 is similar to third embodiment moisture detector 4-3 described above except that fourth embodiment moisture detector 44 includes a third conductor 126 disposed on substrate 104 between first conductor 100 and the portion of second conductor 102 having longitudinal axis 114. Fourth embodiment moisture detector 4-4 also includes a fourth conductor 128 disposed on substrate 104 between first conductor 100 and third conductor 126. Fourth conductor 128 defines a gap 130 intermediate the opposite ends of fourth conductor 128 which are coupled to the portions of second conductor 102 having longitudinal axis 119 and 120 associated therewith. Third and fourth conductors 126 and 128 define longitudinal axes 132 and 134, respectively, that are positioned in spaced relation with longitudinal axis 112 of first conductor 100, e.g. in substantially spaced parallel relation. In this nonlimiting embodiment, the portions of second conductor 102 associated with longitudinal axes 114-118 along with conductors 100, 126 and 128 define zigzag paths along their longitudinal axes. These zigzag paths track each other in substantially spaced parallel relation along their longitudinal axes.

Portions of second conductor 102 spaced from opposite ends of first conductor 100 define longitudinal axes 119 and 120 that are positioned substantially perpendicular to longitudinal axis 112 of first conductor 100. The portions of second conductor 102 associated with longitudinal axes 119 and 120 define mirror image zigzag paths.

Power conductor 106 is connected to first conductor 100 intermediate the ends thereof via gap 103 between the ends of second conductor 102. Power conductor 106 is also connected to third conductor 126 intermediate the ends thereof via gap 130 between the ends of fourth conductor 128. Like the third embodiment moisture detector 4-3, ground conductors 108 and 110 are disposed on substrate 104 and are electrically connected to opposite ends of second conductor 102.

In one nonlimiting embodiment of the present invention, temperature sensor 122 is disposed at or adjacent moisture detector 44, e.g., on substrate 104 in operative relation to, for example, second conductor 102.

Fourth embodiment moisture detector 44 including substrate 104 can be sandwiched between glass plies 10 and 12 in the manner discussed above in connection with second embodiment moisture detector 4-2. Although not required, conductive material 46 can be disposed on substrate 104 in the manner described above in connection with moisture detector 4-2 to avoid undesirable electromagnetic interference from affecting the operation of moisture detector 4-4. Similarly, electrically conductive coating 48 can be utilized with fourth embodiment moisture detector 4-4 including substrate 104 in the manner described above in connection with second embodiment moisture detector 4-2.

Alternatively, substrate 104 can be omitted and the conductors comprising fourth embodiment moisture detector 44 can be disposed directly on one or more surfaces of glass ply 10, glass ply 12 and/or interlayer 14 in any desired arrangement deemed suitable by one of ordinary skill in the art. In one nonlimiting configuration, temperature sensor 122 is disposed on the same surface of glass ply 10, glass ply 12 or interlayer 14 as the conductors of fourth embodiment moisture detector 44. Electrically conductive coating 48 can also be utilized with fourth embodiment moisture detector 4-4 where the conductors thereof are disposed directly on one or more surfaces of glass ply 10, glass ply 12 and/or interlayer 14.

Some exemplary dimensions of fourth embodiment moisture detector 4-4 are shown in FIG. 9. These exemplary dimensions are also applicable to third embodiment moisture detector 4-3. However, these dimensions are not to be construed as limiting the invention.

With reference to FIG. 10, and with continuing reference to all previous figures, the electronic circuitry coupled to electrical conductor 6 of moisture detector 4-1 or 4-2, or to power conductor 106 of moisture detector 4-3 or 4-4 includes a microprocessor 20, a frequency generator 22, a resonant circuit 24, a filter circuit 26, and an analog-todigital converter 28. A windshield wiper system 30 is connected to receive one or more control signals from microprocessor 20, which control the operation of windshield wiper system 30 in a manner to be described hereinafter.

Microprocessor 20 is interfaced with certain electronic hardware, such as ROM memory, RAM memory, I/O buffers, clock circuitry, and the like, which have not been included in FIG. 10 for simplicity of illustration. Microprocessor 20 operates under the control of a software program stored in a memory connected to microprocessor 20. Under the control of this software program, microprocessor 20 causes frequency generator 22 to output an oscillator signal having a predetermined amplitude and a predetermined frequency. In one nonlimiting embodiment, this predetermined frequency is between 300 kHz and 700 kHz, e.g. between 400 kHz and 600 kHz. The oscillator signal is supplied to resonant circuit 24 which is coupled to electrical conductor 6 of moisture detector 4-1 or 4-2, or to power conductor 106 of moisture detector 4-3 or 44. In response to receiving the oscillator signal, resonant circuit 24 outputs a resonator signal to electrical conductor 6 of moisture detector 4-1 or 4-2, or to power conductor 106 of moisture detector 4-3 or 4-4.

In the particular nonlimiting embodiment of the present invention shown in FIG. 10, resonant circuit 24 includes resistor R1 and capacitor C1 connected in series as shown. Electrical conductor 6 of moisture 4-1 or 4-2, or power conductor 106 of moisture detector 4-3 or 4-4 is electrically connected to a node between resistor R1 and capacitor C1.

In addition, filter circuit 26 includes an inductor 11 and a diode D1 connected in series as shown to conduct the resonator signal from resonant circuit 24 toward analog-to-digital converter 28. A capacitor C2 is connected between a side of diode D1 opposite resonant circuit 24 and reference voltage 34. Optionally, an inductor 12 can be connected in parallel with capacitor C2. The output of filter circuit 26 is a rectified and filtered signal that is supplied to digital-to-analog converter 28. Under the control of microprocessor 20, analog-to-digital converter 28 samples the rectified and filtered signal and converts it into an equivalent digital signal, which is sampled by microprocessor 20.

In the following description, moisture detector 4 will be utilized. It is to be understood, however, that any one of moisture detectors 4-1 through 44 can be substituted for moisture detector 4.

In order to detect the presence of moisture on windshield 2, microprocessor 20 causes frequency generator 22 to generate the oscillator signal when no moisture is present on an outward facing surface of windshield 2. Microprocessor 20 then determines the response of moisture detector 4 to the oscillator signal by sampling a first digital signal output by analog-to-digital converter 28 when moisture detector 4 is receiving the oscillator signal. Microprocessor 20 stores this first digital signal for future use.

Next, when moisture, e.g., condensed or diffused liquid such as water, is present on the outward facing surface of windshield 2, microprocessor 20 samples a second digital signal output by analog-to-digital converter 28 when moisture detector 4 is receiving the oscillator signal.

Alternatively, microprocessor 20 can sample the first digital signal when moisture e.g., condensed or diffused liquid such as water, is present on the outward facing surface of windshield 2 and can sample the second digital signal when no moisture is present on the outward facing surface of windshield 2. To this end, the first digital signal, corresponding to the presence or absence of moisture on windshield 2, can be utilized as the basis for determining from the second digital signal when moisture is present on or absent from windshield 2. The use of the first and second digital signals to determine the presence or absence of moisture on windshield 2 will be described hereinafter.

It has been observed that, for a given temperature, the rectified and filtered signal output by filter circuit 26 has a different amplitude when moisture is present on windshield 2 adjacent moisture detector 4. More specifically, the rectified and filtered signal output by filter circuit 26 has an amplitude that increases or decreases to a limit with increasing moisture on windshield 2 adjacent moisture detector 4. For example, in the absence of moisture on windshield 2 adjacent moisture detector 4, the rectified and filtered signal has a first amplitude. However, when moisture in the form of droplets of water is present on windshield 2 adjacent moisture detector 4, the rectified and filtered signal output by filter circuit 26 has a second amplitude different than the first amplitude. Furthermore, when moisture in the form of diffused water is present on windshield 2 adjacent moisture detector 4, the rectified and filtered signal output by filter circuit 26 has a third amplitude different than the first and second amplitudes.

This changing amplitude is caused by the impedance of moisture detector 4, changing due to increasing or decreasing amounts of moisture on windshield 2 adjacent moisture detector 4. More specifically, the impedance of moisture detector 4 decreases in response to increasing amounts of moisture on windshield 2 adjacent moisture detector 4, whereupon the amplitude of the rectified and filtered signal output by filter circuit 26 decreases. Similarly, the impedance of moisture detector 4 increases in response to decreasing amounts of moisture on windshield 2 adjacent moisture detector 4, whereupon the amplitude of the rectified and filtered signal output by filter circuit 26 increases.

The electronic circuitry coupled to moisture detector 4 can detect changes in the impedance thereof due to changes in the moisture on windshield 2 adjacent moisture detector 4 between no moisture and diffused liquid.

Next, microprocessor 20 compares the first digital signal to the second digital signal to determine the amount of moisture that is present on windshield 2 adjacent moisture detector 4. More specifically, microprocessor 20 takes the difference between the first and second digital signals and determines therefrom the presence of moisture, and in one nonlimiting embodiment, an amount of moisture that is present on windshield 2 adjacent moisture detector 4. Based on this determination, microprocessor 20 outputs a control signal to windshield wiper system 30 for controlling the operation thereof based on the presence and/or amount of moisture on windshield 2.

With reference to FIG. 11, and with continuing reference to all previous figures, windshield wiper system 30 includes a windshield wiper motor control 36 which receives the control signal from microprocessor 20, and a windshield wiper motor 38 which is coupled to a windshield wiper blade 40 disposed on windshield 2. As discussed above, the control signal supplied by microprocessor 20 to windshield wiper motor control 36 is related to the difference between the first and second digital signals sampled by microprocessor 20. In order to control windshield wiper system 30 in accordance with the amount of moisture on windshield 2 adjacent moisture detector 4, the numerical range of digital difference values that can be processed by microprocessor 20 is divided into sections based on the desired control of windshield wiper system 30. For example, if the range of digital difference values is divided into two sections, the section corresponding to the upper numerical range of difference values corresponds to operating windshield wiper system 30 at a high speed while the lower numerical range of difference values corresponds to operating windshield wiper system 30 at a low speed. Thus, if a difference value between a current sample of the second digital signal and the first digital signal is within the upper numerical range of difference values, microprocessor 20 outputs the control signal which causes windshield wiper motor control 36 to control windshield wiper motor 38 to operate windshield wiper blade 40 at a high speed. Similarly, if the difference value between the current sample of the second digital signal and the first digital signal is within the lower numerical range of difference values, microprocessor 20 outputs the control signal which causes windshield wiper motor control 36 to control windshield wiper motor 38 to operate windshield wiper blade 40 at a low speed.

Various other modes of operation of windshield wiper system 30 can also be enabled by microprocessor 20 and windshield wiper motor control 36 as a function of the difference value between a current sample of the second digital signal and the first digital signal. These modes can include: a single pulse mode where windshield wiper blade 40 is caused to wipe windshield 2 once, e.g., to remove dew or mist from windshield 2; a continuous duty cycle pulse mode, e.g., where there is a steady accumulation of water droplets on windshield 2, but the accumulation is not sufficient enough to warrant continuous operation of windshield wiper system 30 at low speed; and a variable duty cycle pulse mode where wiping of windshield 2 by windshield wiper blade 40 varies as a function of the amount and/or rate of moisture accumulation on windshield 2.

Microprocessor 20 can be configured to output two or more different control signals which cause windshield wiper system 30 to implement two or more of the above modes of operation in response to varying amounts of moisture on windshield 2. In the absence of moisture on windshield 2, microprocessor 20 can cause windshield wiper system 30 to either discontinue or not initiate the wiping of windshield 2 with windshield wiper blade 40.

It has been observed that the temperature of windshield 2 can affect the sensitivity of each embodiment moisture detector 4 discussed above. Accordingly, a temperature sensor, like temperature sensor 122 described above, can be disposed at or adjacent moisture detector 4, e.g., in operative relation to the corresponding moisture detector 4 on flexible substrate 16 or 104 disposed on windshield 2, e.g. on one of the surfaces of glass ply 10, glass ply 12, plastic interlayer 14 or flexible substrates 16 or 104, in order to detect the temperature of windshield 2 at or adjacent moisture detector 4.

In operation, microprocessor 20 determines the response of moisture detector 4 to the oscillator signal output by frequency generator 22 by sampling one or more digital signals output by analog-to-digital converter 28 when moisture detector 4 is receiving the oscillator signal. On or about the time microprocessor 20 samples each digital signal output by analog-to-digital converter 28, microprocessor 20 measures a property of temperature sensor 122 that varies in response to changes in temperature at or adjacent temperature sensor 122. As a function of this measured property, microprocessor 20 applies a correction factor to each digital signal received by microprocessor 20 from analog-to-digital converter 28. The correction factor applied to each digital signal received by microprocessor 20 adjusts the value of the digital signal based on the measured temperature at or adjacent moisture detector 4, whereupon the control signal output by microprocessor 20 to windshield wiper system 30 is adjusted for temperature, thereby avoiding inadvertent operation or non-operation of windshield wiper system 30. Thus, windshield wiper system 30 is operated as a function of the measured properties of moisture detector 4 and temperature sensor 122.

In one nonlimiting embodiment, temperature sensor 122 is a thermistor that has a resistance that changes as a function of the temperature. Alternatively, temperature sensor 122 can be a bimetallic junction temperature sensor, or a conductor having a resistance that changes as a function of the temperature, or an optical temperature sensor that optically detects the temperature at or adjacent moisture detector 4 by optical means, and which outputs to microprocessor 20 a signal indicative of the thus detected temperature.

Figure 12A:
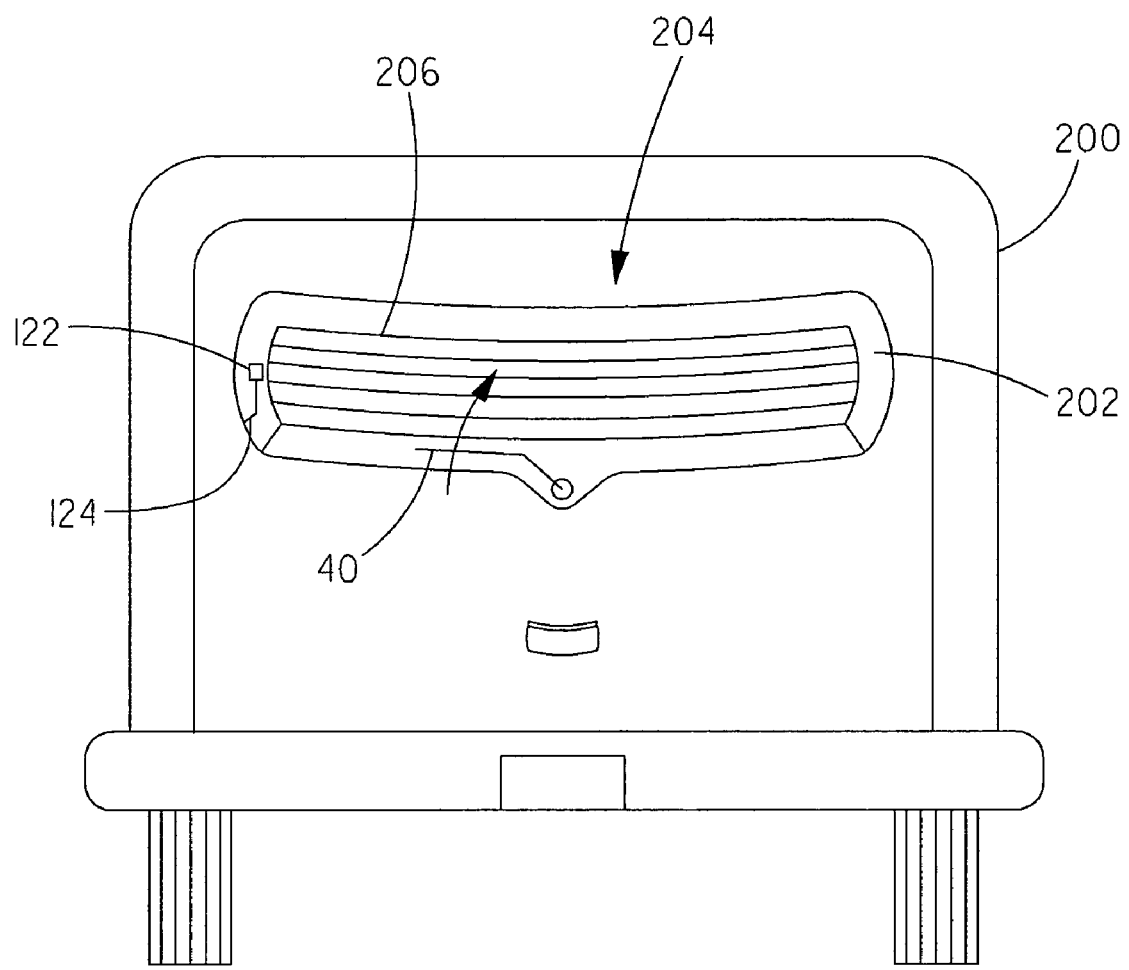
FIG. 12a is a back view of a vehicle having a back window with a heated grid having one or more resistive wires that can be utilized either for heating the back window or as a fifth, nonlimiting embodiment of a moisture detector for detecting the accumulation of moisture on the back window.

With reference to FIG. 12a, often, a vehicle 200, such as an SUV, a minivan, a hatchback, and the like, includes a windshield wiper system, such as windshield wiper system 30, on a rear window 202 (or backlite) thereof. This windshield wiper system is operative for controlling the motion of a wiper blade, like wiper blade 40, for removing an accumulation of moisture on the exterior of a rear window 202. Often, rear window 202 also includes a heating grid 204 comprised of one or more resistive wires 206 adhered to the inside surface of rear window 202 in a manner known in the art. As shown in FIG. 12a, the resistive wires 206 comprising heating grid 204 typically run from side-to-side of rear window 202 in spaced relation. However, this is not to be construed as limiting the invention since the use of any suitable and/or desirable configuration of resistive wires 206 to form heating grid 204 is envisioned. Resistive wires 206 of heating grid 204 are typically used to heat rear window 202 to remove or avoid the accumulation of moisture, on an exterior surface of rear window 202 in a manner know in the art.

Figure 12B:
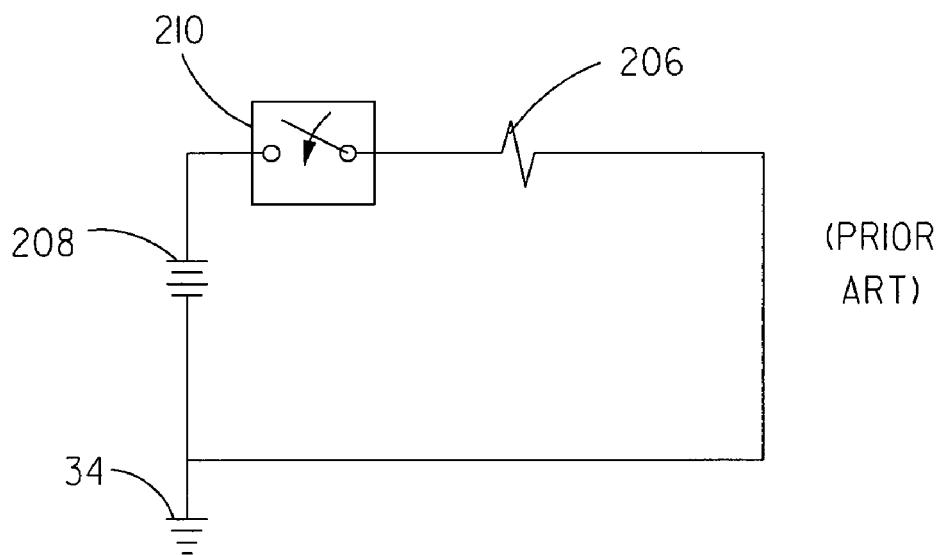
FIG. 12b is a simplified circuit diagram of a prior art circuit for heating the back window of the vehicle shown in FIG. 12a via the one or more resistive wires.

With reference to FIG. 12b and with continuing reference to FIG. 12a, the resistive wires 206 of heating grid 204 are shown schematically in FIG. 12b as a resistor. In accordance with the prior art, the resistor depicting resistive wires 206 in FIG. 12b is connected to a battery 208 of vehicle 200 via a switch 210, typically disposed in a dashboard of vehicle 200. As is also well-known in the art, battery 208 may be coupled to an engine driven alternator (not shown) of vehicle 200 which is operative for charging battery 208 during operation of vehicle 200.

In response to closure of switch 210, power from battery 208 is applied to resistive wires 206 of heating grid 204. In response to a flow of current therein, resistive wires 206 generate and dissipate heat into the body of rear window 202. This heat dissipated into rear window 202 facilitates the removal of moisture accumulated on the exterior surface of rear window 202 or avoids the accumulation of moisture on the exterior surface of rear window 202 in a manner known in the art.

Figure 13:
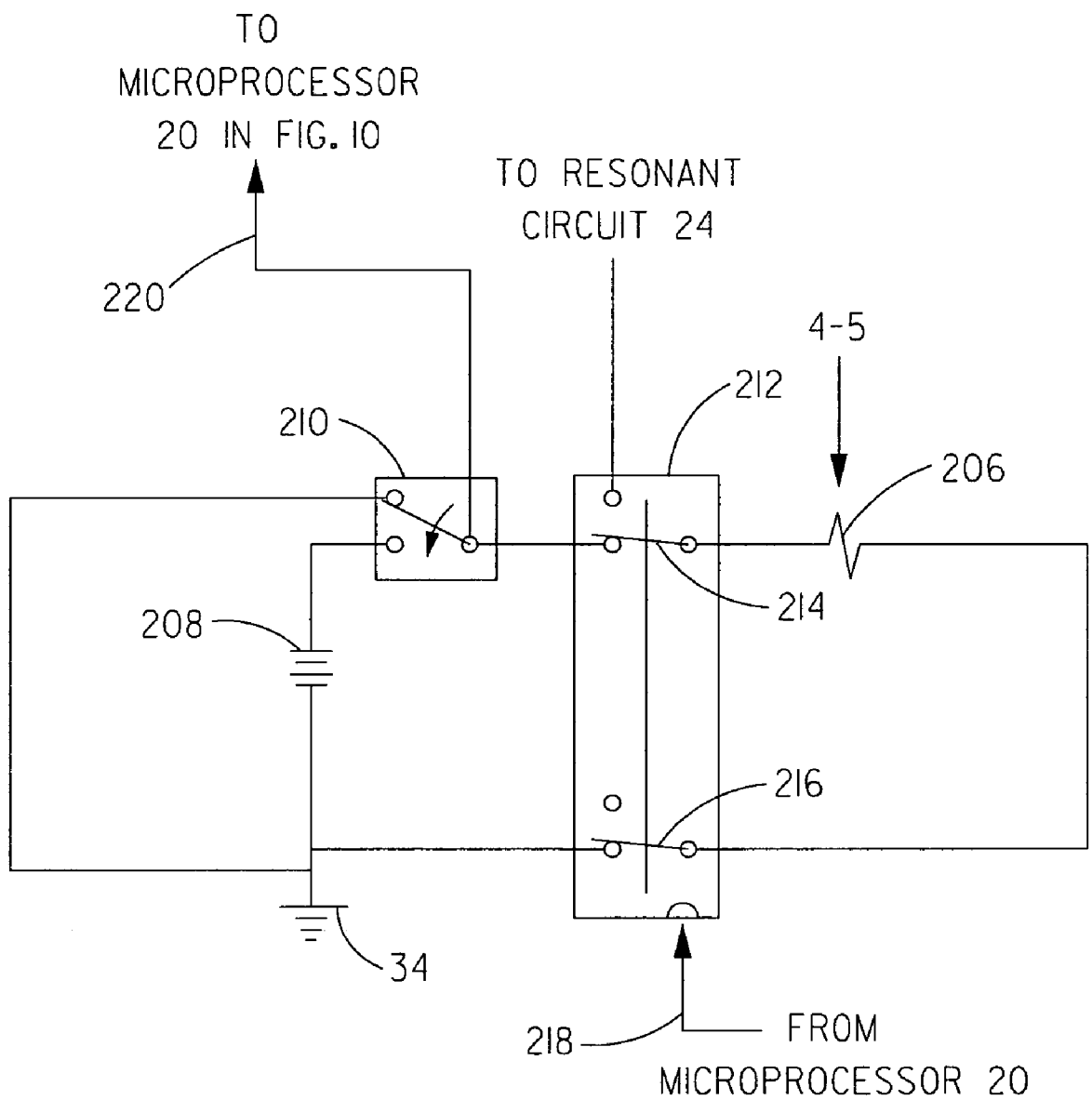
FIG. 13 is a simplified circuit diagram of the circuit of FIG. 12b modified in an exemplary, non-limiting manner to enable the microprocessor of the circuitry of FIG. 10 to switch the resistive wires between a first use as resistive heating elements and a second use as the fifth embodiment moisture detector.

With reference to FIG. 13, in accordance with the present invention, a fifth embodiment moisture detector 4-5 can comprise one or more of the resistive wires 206 of heating grid 204. Thus, said one or more resistive wires 206 can serve the dual purpose of heating element(s) for removing or avoiding an accumulation of moisture on the exterior surface of rear window 202, and a moisture detector for detecting an accumulation of moisture on the exterior of rear window 202. In one exemplary, nonlimiting embodiment of utilizing one or more resistive wires 206 as the fifth embodiment moisture detector 4-5, a switch 212, e.g., a double-pole double-throw switch, has a first pole 214 switchable between a first position wherein the one or more resistive wires 206 of heating grid 204 can receive electrical power from battery 208 in response to closure of switch 210, and a second position wherein said one or more resistive wires 206 are coupled to resonant circuit 24 of moisture detector 4 shown in FIG. 10. Desirably, switch 212 also includes another pole 216 switchable between a first position, wherein said one or more resistive wire(s) 206 of heating grid 204 are coupled to reference voltage 34, and a second position, wherein said resistive wires 206 are isolated from reference voltage 34. However, this is not to be construed as limiting the invention.

In FIGS. 12b and 13, reference voltage 34 is shown as being at the same potential as the negative terminal of battery 208. However, this is not to be construed as limiting the invention.

Desirably, poles 214 and 216 of switch 212 are configured to operate in concert whereupon poles 214 and 216 switch together between their respective first positions and second positions under the control of microprocessor 20 via a control line 218 that extends between microprocessor 20 and a control input of switch 212. More specifically, via control line 218, microprocessor 20 can cause poles 214 and 216 to switch from their first positions, where the one or more resistive wires 206 are utilized as heating elements, to their second positions, where said one or more resistive wires 206 are utilized as moisture detector 4-5 for detecting the accumulation of moisture on the exterior surface of rear window 202.

When poles 214 and 216 are in their second positions, an oscillator signal can be applied to said one or more resistive wires 206 via resonant circuit 24 under the control of microprocessor 20. When no moisture is present on the outward facing surface of rear window 202, microprocessor 20 determines the response of moisture detector 4-5 to the oscillator signal by sampling a first digital signal output by analog-to-digital converter 28 when fifth embodiment moisture detector 4-5 is receiving the oscillator signal. Microprocessor 20 then stores this first digital signal for future use.

Next, microprocessor 20 samples a second digital signal output by analog-to-digital converter 28 when moisture detector 4-5 is receiving the oscillator signal and when moisture, e.g., condensed or diffused liquid such as water, frost or snow, is present on the outward facing surface of rear window 202. Alternatively, microprocessor 20 can sample the first digital signal when moisture is present on the outward facing surface of rear window 202 and can sample the second digital signal when no moisture is present on the outward facing surface of rear window 202.

Next, microprocessor 20 compares the first digital signal to the second digital signal to determine if moisture is present on windshield 2 adjacent moisture detector 4-5. More specifically, microprocessor 20 takes the difference between the first and second digital signals and determines therefrom whether moisture is present on rear window 202 adjacent moisture detector 4-5. Based on this determination, microprocessor 20 can output a control signal to the windshield wiper system operative for controlling the movement of the wiper blade on rear window 202 based on the presence of moisture on an exterior surface thereof.

Typically, rear window 202 is a single glass ply. However, this is not to be construed as limiting the invention since it is envisioned that rear window 202 can be formed from two or more glass plies, with each pair of glass plies having a plastic interlayer therebetween to form rear window 202 as a unitary structure, like windshield 2 shown in FIGS. 1 and 2.

Typically, resistive wires 206 are disposed on the inside surface of rear window 202. However, this is not to be construed as limiting the invention since it is envisioned that resistive wires 206 can be positioned on any surface of rear window 202, including an inner surface of rear window 202 when rear window 202 is made from two or more glass plies bonded together to form a unitary structure, without affecting the use of resistive wires 206 as heating element(s) and a moisture detector.

FIG. 12a shows that a temperature sensor, like temperature sensor 122 can be positioned on rear window 202 thereby enabling microprocessor 20 determine a property of said temperature sensor that varies in response to changes in temperature at or adjacent heating grid 204. As a function of this measured property, microprocessor 20 can apply a correction factor to each digital signal received by microprocessor 20 from analog-to-digital converter 28. This correction factor adjusts the value of the digital signal based on the measured temperature at or adjacent moisture detector 4 whereupon the control signal output by microprocessor 20 to the windshield wiper system controlling the movement of the wiper blade on rear window 202 is adjusted for temperature, thereby avoiding inadvertent operation or non-operation of the windshield wiper system that is operative for controlling the motion of the wiper blade on rear window 202.

While the temperature sensor in FIG. 12a is illustrated as being outside of the wiping area of wiper blade 40, it is desirable that the temperature sensor be positioned in the path of the wiper blade to detect a temperature in said path. However, this is not to be construed as limiting the invention.

Typically, the accumulation of fine mist and the response time of having moisture cleared off of rear window 202 by the wiper blade is not as important on rear window 202 as it would be on the front windshield of vehicle 200. Accordingly, the control signal output by microprocessor 20 that causes the wiper blade to wipe moisture from rear window 202 can be set to be related to a larger difference between the first and second digital signals sampled by microprocessor 20 from the one or more resistive wires 206 acting as the fifth embodiment moisture detector 4-5.

If desired, microprocessor 20 can be operative for detecting when the one or more resistive wires 206 is being utilized for heating rear window 202. For example, microprocessor 20 can be operative for detecting the open and closed states of switch 210 via a line 220 coupled between microprocessor 20 and switch 210. In response to detecting that switch 210 is in its open state (shown in FIG. 13), microprocessor 20 can utilize the one or more resistive wires 206 as the fifth embodiment moisture detector 4-5 under the assumption that the one or more resistive wires are not being utilized for heating rear window 202. In contrast, in response to detecting switch 210 is in its closed state, microprocessor 20 does not utilize the one or more resistive wires 206 as the fifth embodiment moisture detector 4-5 under the assumption that the one or more resistive wires 206 are already being utilized to heat rear window 202.

Also or alternatively, microprocessor 20 can be operative for utilizing the one or more resistive wires 206 as the fifth embodiment moisture detector 4-5 regardless of whether switch 210 is in its open or closed state. Specifically, at suitable times, microprocessor 20 can cause poles 214 and 216 of switch 212 to switch to their respective second positions for a time sufficient for microprocessor 20 to sample the output of analog-to-digital converter 28 when said one or more resistive wires 206, acting as the fifth embodiment moisture detector 4-5, are receiving the oscillator signal. Thereafter, microprocessor 20 can cause poles 214 and 216 to return to their respective first positions whereupon said one or more resistive wires 206 can be utilized (or nor utilized) as heating element(s) when switch 210 is in its closed (or open) state.

The illustration of the simplified circuit diagram of FIG. 13, especially switch 212, for switching one or more resistive wires 206 of heating grid 204 between use as heating element(s) for heating rear window 202 and the fifth embodiment moisture sensor 4-5 is not to be construed as limiting the invention since it is envisioned at any suitable and/or desirable means for switching the functions of the one or more resistive wires 206 is envisioned. Moreover, the illustration of switch 210 in FIGS. 12b and 13 is not to be construed as limiting the invention.

Figure 14A:
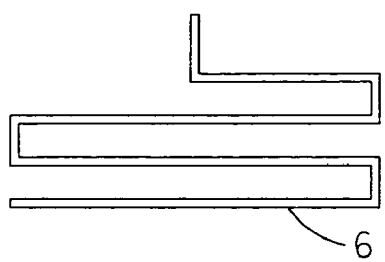
FIGS. 14a-14d show alternate embodiments of the electrical conductor of the first and second embodiment moisture detectors.
Figure 14B:
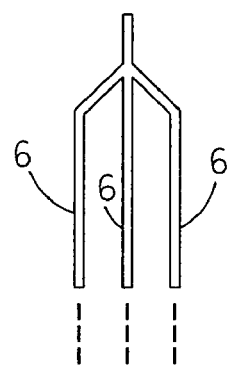
Figure 14C:
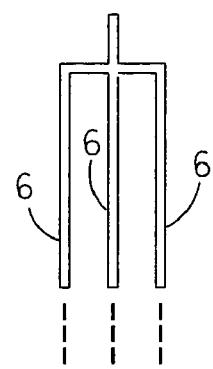
Figure 14D:
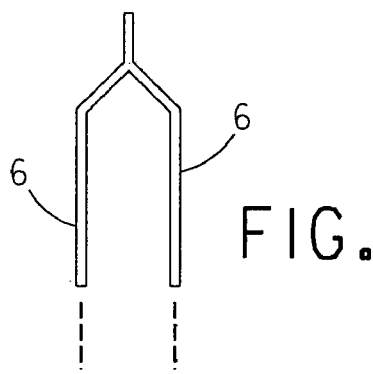

With reference to FIGS. 14a-14d, various different embodiments of electrical conductor 6 of the first and second embodiments of moisture detectors 4-1 and 4-2 are illustrated. FIG. 14a and FIG. 5 show electrical conductor 6 formed in a serpentine pattern. FIGS. 14b and 14c show three parallel electrical conductors 6 extending in spaced relation from a common node. As indicated by the dashed extensions of electrical conductors 6 in FIGS. 14b and 14c, electrical conductors 6 can be formed to any desired length. Lastly, in FIG. 14d, two parallel electrical conductors 6 extend in spaced relation from a common node. Again, the dashed lines extending from electrical conductors 6 in FIG. 12d indicate that electrical conductors 6 can have any desired length.

The present invention has several advantages over prior art systems for detecting moisture. These advantages include moisture detector 4 being essentially invisible to the naked eye from about one meter; moisture detector 4 can be disposed in a clear or non-transparent part of windshield 2; moisture detector 4 is not sensitive to dirt; moisture detector 4 can detect the presence of moisture over a larger area than prior art sensors of comparable size; moisture detector 4 is useful with substrates of various thickness and composition; moisture detector 4 is more uniformly responsive than prior art sensors; and the present invention can more readily detect the presence of moisture droplets of smaller size, e.g., dew or mist, on windshield 2 than the prior art systems for detecting moisture.

Figure 15:
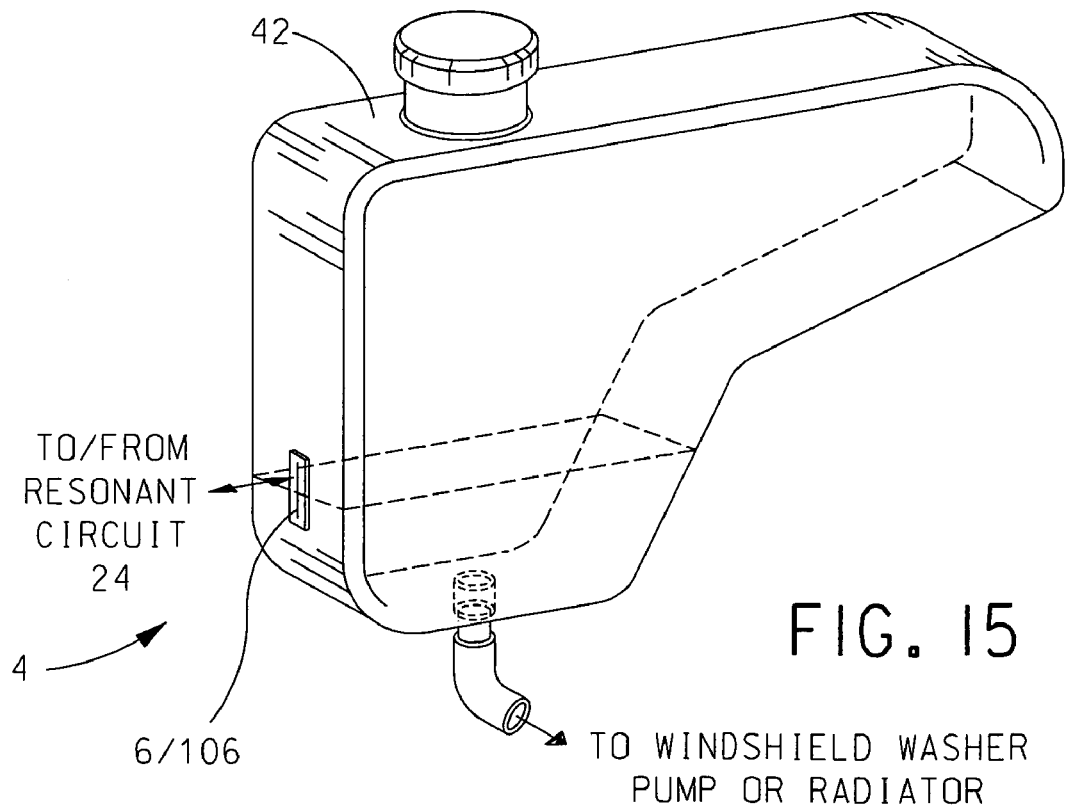
FIG. 15 is an isolated perspective view of a fluid reservoir of a vehicle including any one of the first through fourth embodiment moisture detectors disposed thereon.

With reference to FIG. 15 and with reference back to FIG. 10, the present invention can also be utilized to detect a level of one or more fluids, such as the level of a fluid in a vehicle. Specifically, moisture detector 4 can be mounted on an electrically and magnetically nonconductive fluid reservoir 42. Preferably, moisture detector 4 is mounted on an exterior of fluid reservoir 42 adjacent a lower end thereof. However, this is not to be construed as limiting the invention. Fluid reservoir 42 can be configured to receive windshield washer fluid, radiator fluid, or any other fluid utilized by a vehicle, the level of which fluid can be measured utilizing moisture detector 4 and the electronic circuitry shown in FIG. 15.

In order to detect the level of fluid in fluid reservoir 42, the oscillator signal is supplied to electrical conductor 6 or 106 of moisture detector 4 when no fluid is received in fluid reservoir 42. A first response of moisture detector 4 is sampled and stored for later use. At suitable times when fluid is received in the fluid reservoir, plural second responses of moisture detector 4 to the oscillator signal are sampled. Each second response is compared to the first response. When a second response has a predetermined relation to the first response, the electronic circuitry outputs a corresponding control signal which activates a suitable indicator, e.g., "check washer fluid", "check radiator fluid", etc.

It is to be appreciated that decreasing the fluid level in fluid reservoir 42 decreases the difference between the first response and the second response of moisture detector 4. Thus, when the second response has the predetermined relation to the first response indicative of the fluid level decreasing to a predetermined level, the electronic circuitry outputs the control signal. To facilitate detecting the change in the resonant frequency of moisture detector 4, the predetermined frequency of the oscillator signal can be selected to optimize the change in impedance of moisture detector 4 in response to the presence of fluid in fluid reservoir 42. Similar comments apply in respect of the change in resonant frequency of moisture detector 4 due to the presence of moisture on windshield 2.

When a vehicle includes multiple moisture detectors 4, a multiplexer (not shown) can be connected between each moisture detector 4 and the electronic circuitry shown in FIG. 15. Under the control of microprocessor 20, the multiplexer can selectively connect the electronic circuitry to each moisture detector 4 for supplying the oscillator signal at an appropriate frequency to each moisture detector 4 and for detecting the response of each moisture detector 4 to the supplied oscillator signal. Preferably, under the control of the software program, microprocessor 20 can adjust the frequency of the oscillator signal output by frequency generator 22 to optimize the change in the resonant frequency of each moisture detector 4 to detect the presence or absence of a particular fluid.

The invention has been described with reference to several nonlimiting embodiments. Obvious modifications and alterations will occur to others upon reading and understanding the preceding detailed description. For example, while described in connection with the detection of moisture on windshield 2, the present invention can also be utilized to detect moisture on surfaces of rigid or flexible substrates utilized in connection with other applications. Similarly, while described in connection with detection of fluid levels in a fluid reservoir 42 mounted on a vehicle, the present invention can also be utilized to detect the level of a fluid received in a fluid reservoir utilized in other applications. Moreover, while described in connection with the control of windshield wiper system 30, microprocessor 20 can also be utilized to control a vehicle headlamp system, a vehicle windshield dehumidification system and/or any other vehicle or non-vehicle based system that it is desired to control as a function of the presence of moisture on a substrate. Still further, while the various components of the electronic circuitry are preferably connected by conductors, it should be appreciated that suitable signals can be conveyed between two or more of these components via suitable radio frequency (RF) and/or optical signal means. Microprocessor 20 can also be configured to record for subsequent retrieval and display, the days when moisture is detected on a substrate and/or the extent of operation of windshield wiper system 30. This information can then be used for information purposes, e.g., to determine the number of days in a month it rains, and/or to estimate when blades of the windshield wiper system 30 may require replacement. Moreover, it is to be appreciated that the description of analog-to-digital converter 28 as being operative for converting analog signals from filter circuit 26, temperature sensor 122 and switch 210 into corresponding digital signals is not to be construed as limiting the invention since it is envisioned that the conversion of each analog signal into a corresponding digital signal for processing by microprocessor 20 can occur in any suitable and/or desirable manner, such as, without limitation, a separate analog-to-digital converter under the control of microprocessor 20, the combination of a multiplexer (not shown) under the control of microprocessor 20 for switching each analog signal to the input of analog-to-digital converter 28, or some combination of at least one multiplexer and two or more analog-to-digital converters. Lastly, the illustration in FIG. 10 of microprocessor 20 and analog-to-digital converter 28 being separate components is not to be construed as limiting the invention since it is envisioned that the functions of microprocessor 20 and one or more analog-to-digital converter 28 can be incorporated into a single component, e.g., a single integrated circuit. It is intended that the invention be construed as including all such modifications and alterations insofar as they come within the scope of the appended claims or the equivalents thereof.

The invention claimed is:

1. A moisture detection system comprising:
an electrical conductor disposed on a surface of a substrate and having a resonant frequency that varies as a function of an amount of moisture present adjacent the electrical conductor;
an oscillator which outputs an oscillator signal at a predetermined amplitude and a predetermined frequency;
a resonator circuit coupled to the electrical conductor and responsive to the oscillator signal for outputting a resonator signal having an amplitude related to the resonant frequency of the electrical conductor;
a filter circuit responsive to the resonator signal for outputting a rectified and filtered signal;
an analog-to-digital converter responsive to the rectified and filtered signal for outputting a digital signal related to the rectified and filtered signal;
a sensor having a property that varies as a function of a temperature at or adjacent the electrical conductor; and
a controller responsive to the digital signal and the property of the sensor for causing another system to operate as a function thereof.

2. The system of claim 1, wherein:
the other system is a wiper system that is responsive to the controller for adjusting a rate moisture is removed from adjacent the electrical conductor as a function of an amount of moisture present adjacent the electrical conductor and/or a rate moisture accumulates adjacent the electrical conductor.

3. The system of claim 1, wherein the substrate is a flexible substrate having either (i) a ground conductor disposed on the flexible substrate at least partially surrounding the electrical conductor or (ii) a conductive material disposed on a surface of the flexible substrate opposite the electrical conductor, said conductive material having a form that defines a faraday shield.

4. The system of claim 1, wherein:
the resonator circuit includes a capacitor connected between the electrical conductor and a reference voltage and a resistor connected between the oscillator and the electrical conductor side of the capacitor; and/or
the filter circuit includes a diode connected to conduct current from the resonator toward the analog-to-digital converter and a capacitor connected between an end of the diode adjacent the analog-to-digital converter and the reference voltage.

5. A moisture detector system comprising:
means disposed on a substrate for conducting electrical current, the conducting means having a resonant frequency that changes as a function of moisture adjacent the conducting means;
an oscillator for outputting to the conducting means an oscillator signal having a predetermined frequency and a first amplitude;
means responsive to the oscillator signal for outputting a resonator signal having a second amplitude related to the resonant frequency of the conducting means, wherein the second amplitude is different than the first amplitude;
means having a property whose value varies as a function of a temperature at or adjacent the conducting means; and
means responsive to the resonator signal and the value of the property for outputting a control signal having a value related to the second amplitude of the resonator signal.

6. The moisture detector of claim 5, further including a wiper system responsive to the control signal for wiping moisture from adjacent the conducting means based on an amount of moisture adjacent the conducting means and/or a rate moisture accumulates adjacent the conducting means.

7. The moisture detector of claim 5, wherein:
the substrate is a flexible substrate that is coupled to a sheet; and
the conducting means has a resonant frequency that changes as a function of moisture on the sheet.

8. The moisture detector of claim 7, wherein the conducting means includes one or more lines of electrically conductive material disposed on the flexible substrate.

9. The moisture detector of claim 7, wherein the flexible substrate further includes (i) a ground conductor disposed on the flexible substrate at least partially surrounding the conducting means or (ii) a conductive material disposed on a surface of the flexible substrate opposite the conducting means, said conductive material having a form that defines a faraday shield.

10. A method of moisture detection comprising:
(a) providing a substrate having an electrical conductor disposed thereon;
(b) stimulating the electrical conductor with an oscillator signal in the absence of moisture adjacent the electrical conductor;
(c) detecting a value of a temperature dependent property acquired from a location at or adjacent the electrical conductor on or about the time step (b) is performed;
(d) determining a first amplitude of the electrical conductor to the stimulation in step (b) as a function of the value of the temperature dependent property detected in step (c);
(e) stimulating the electrical conductor with the oscillator signal when moisture is present adjacent the electrical conductor;
(f) detecting the value of the temperature dependent property on or about the time step (e) is performed;
(g) determining a second amplitude of the electrical conductor to the stimulation in step (e) as a function of the value of the temperature dependent property detected in step (f), wherein the second amplitude is different than the first amplitude due to a change in resonant frequency of the electrical conductor in response to the presence of moisture adjacent the electrical conductor; and (h) determining a difference between the first amplitude and the second amplitude, wherein the difference is related to the amount of moisture present adjacent the electrical conductor.

11. The method of claim 10, wherein the detected temperature dependent property is physically or optically detected.

12. The method of claim 11, wherein the physically detected property is voltage, current or resistance.

13. The moisture detection system of claim 10, wherein the detected temperature dependent property is:
a potential output by a bi-metallic junction acting as the temperature sensor;
a resistance of a thermistor or a conductor acting as the temperature sensor; or
a signal output by an optical temperature sensor acting as the temperature sensor.

14. The method of claim 10, further including removing moisture from adjacent the electrical conductor at a rate related to the difference between the first amplitude and the second amplitude.

15. The method of claim 10, further including sandwiching the substrate between at least two sheets of glass.

16. The method of claim 15, further including providing shielding means on (i) the substrate and/or (ii) at least one of the sheets of glass.

17. A moisture detection system comprising:
a substrate;
an electrical conductor disposed on the substrate;
means for stimulating the electrical conductor with an oscillator signal;
means for determining a temperature at or adjacent the electrical conductor; and
means responsive to the oscillator signal, the electrical conductor and the determined temperature for determining temperature corrected changes in a resonant frequency of the electrical conductor in response to changes in an amount of moisture disposed adjacent the electrical conductor.

18. The system of claim 17, further including:
means for removing an accumulation of moisture on the sheet; and
means responsive to the determining means for controlling when the removing means removes the accumulation of moisture from the sheet.

19. A method of moisture detection comprising:
correcting a value of a signal generated in response to the presence of moisture on a substrate as a function of a temperature determined at or adjacent the substrate; and
controlling a system as a function of the corrected signal.

20. A method of moisture detection comprising:
generating a signal having a value related to an amount of moisture on a substrate;
combining the signal with a correction factor related to a temperature determined at or adjacent the substrate; and
controlling a system as a function of the combination.

21. A moisture detection system comprising:
a substrate;
a resistive conductor disposed on the substrate;
a source of DC power;
means for generating an AC oscillator signal;
means for applying the DC power and the AC oscillator signal one at a time to the resistive conductor; and
means responsive to the application of the oscillator signal to the resistive conductor for determining changes in a resonant frequency of the resistive conductor in response to changes in an amount of moisture disposed adjacent the resistive conductor.

22. The system of claim 21, further including:
means for removing an accumulation of moisture on the sheet; and
means responsive to the determining means for controlling when the removing means removes the accumulation of moisture from the sheet.

23. A method of moisture detection comprising:
(a) connecting a resistive conductor to a source of DC power;
(b) disconnecting the resistive conductor from the source of DC power;
(c) connecting the resistive conductor to an AC signal source;
(d) in response to the application of the AC signal source, determining a change in a resonant frequency of the resistive conductor related to a change in an amount of moisture adjacent the resistive conductor; and
(e) removing moisture from adjacent the resistive conductor as a function of the change in the resonant frequency thereof.

24. The method of claim 23, wherein step (e) includes removing moisture from adjacent the resistive conductor as a function of a temperature adjacent the resistive conductor.

* * * * *